(12) United States Patent
Hostetler et al.

(10) Patent No.: US 8,222,257 B2
(45) Date of Patent: Jul. 17, 2012

(54) PHOSPHONO-PENT-2-EN-1-YL NUCLEOSIDES AND ANALOGS

(75) Inventors: Karl Y. Hostetler, Del Mar, CA (US); James R. Beadle, San Diego, CA (US); Hyunah Choo, Seoul (KR)

(73) Assignee: The Regents of the University of California, Oakland, CA (US)

( * ) Notice: Subject to any disclaimer, the term of this patent is extended or adjusted under 35 U.S.C. 154(b) by 841 days.

(21) Appl. No.: 11/887,502

(22) PCT Filed: Mar. 30, 2006

(86) PCT No.: PCT/US2006/012117
§ 371 (c)(1),
(2), (4) Date: Jan. 14, 2009

(87) PCT Pub. No.: WO2006/137953
PCT Pub. Date: Dec. 28, 2006

(65) Prior Publication Data
US 2009/0215726 A1    Aug. 27, 2009

Related U.S. Application Data

(60) Provisional application No. 60/667,740, filed on Apr. 1, 2005.

(51) Int. Cl.
| | |
|---|---|
| *A01N 43/54* | (2006.01) |
| *A01N 43/90* | (2006.01) |
| *A61K 31/522* | (2006.01) |
| *A61K 31/52* | (2006.01) |
| *A61K 31/505* | (2006.01) |
| *C07D 245/00* | (2006.01) |
| *C07D 225/02* | (2006.01) |
| *C07D 487/00* | (2006.01) |
| *C07D 239/02* | (2006.01) |
| *C07D 475/00* | (2006.01) |
| *C07D 473/00* | (2006.01) |
| *C07F 9/02* | (2006.01) |

(52) U.S. Cl. .................. 514/256; 514/258.1; 514/263.2; 514/263.3; 514/263.37; 514/263.4; 514/269; 514/274; 540/460; 540/463; 540/473; 544/243; 544/298; 544/322; 544/334; 544/256; 544/264; 544/265; 544/272; 544/276; 544/277

(58) Field of Classification Search .................. 514/256, 514/258.1, 263.2, 263.3, 263.37, 263.4, 269, 514/274; 540/460, 463, 473; 544/243, 298, 544/322, 334, 256, 264, 265, 272, 276, 277
See application file for complete search history.

(56) References Cited

U.S. PATENT DOCUMENTS

| | | |
|---|---|---|
| 3,536,809 A | 10/1970 | Applezweig |
| 3,598,123 A | 8/1971 | Zaffaroni |
| 3,710,795 A | 1/1973 | Higuchi et al. |
| 3,845,770 A | 11/1974 | Theeuwes et al. |
| 3,916,899 A | 11/1975 | Theeuwes et al. |
| RE28,819 E | 5/1976 | Thompson |
| 4,008,719 A | 2/1977 | Theeuwes et al. |
| 4,044,126 A | 8/1977 | Cook et al. |
| 4,328,245 A | 5/1982 | Yu et al. |
| 4,358,603 A | 11/1982 | Yu |
| 4,364,923 A | 12/1982 | Cook et al. |
| 4,409,239 A | 10/1983 | Yu |
| 4,410,545 A | 10/1983 | Yu et al. |
| 4,414,209 A | 11/1983 | Cook et al. |
| 5,033,252 A | 7/1991 | Carter |
| 5,052,558 A | 10/1991 | Carter |
| 5,059,595 A | 10/1991 | Le Grazie |
| 5,073,543 A | 12/1991 | Marshall et al. |
| 5,120,548 A | 6/1992 | McClelland et al. |
| 5,323,907 A | 6/1994 | Kalvelage |
| 5,354,556 A | 10/1994 | Sparks et al. |
| 5,591,767 A | 1/1997 | Mohr et al. |
| 5,639,476 A | 6/1997 | Oshlack et al. |
| 5,639,480 A | 6/1997 | Bodmer et al. |
| 5,674,533 A | 10/1997 | Santus et al. |
| 5,709,874 A | 1/1998 | Hanson et al. |
| 5,733,566 A | 3/1998 | Lewis |
| 5,739,108 A | 4/1998 | Mitchell |
| 5,759,542 A | 6/1998 | Gurewich |
| 5,840,674 A | 11/1998 | Yatvin et al. |
| 5,860,957 A | 1/1999 | Jacobsen et al. |
| 5,891,474 A | 4/1999 | Busetti et al. |

(Continued)

FOREIGN PATENT DOCUMENTS

| | | |
|---|---|---|
| WO | WO 96/40088 | 12/1996 |
| WO | WO 01/47883 | 7/2001 |
| WO | WO 2005/000308 | 1/2005 |

OTHER PUBLICATIONS

Phadtare et al. 1991, "Unsaturated analogues of acyclic nucleoside phosphonates: an unusual arbuzov reaction with unactivated triple bond." Nucleosides and Nucleotides, vol. 10 (1-3), pp. 275-278.*
Biswal, et al., 2005, "Crystal Structures of the RNA-dependent RNA Polymerase Genotype 2a of Hepatitis C Virus Reveal Two Conformations and Suggest Mechanisms of Inhibition by Non-nucleoside Inhibitors," *J. Biol. Chem.* 289, 18202-18210.
Bryant, et al., 2001, "Amtovora; :=Mic;epsodes S[ecofoc fpr Je[atots B Viruns Infection," *Antimicrobial Agents and Chemotherapy*, vol. 45, No. 1, 229-235.
Buchwald, et al., 1980, "Long-term, continuous intravenous heparin administration by an implantable infusion pump in ambulatory patients with recurrent venous thrombosis," *Surgery* 88:507.
Chan, et al., 2004, "Discovery of thiophene-2-carboxylic acids as potent inhibitors of HCV NS5B polymerase and HCV subgenomic RNA replication. Part 2: Tertiary amides," *Bioorg. Med. Chem. Lett.* 14:797-800.

(Continued)

*Primary Examiner* — Sreeni Padmanabhan
*Assistant Examiner* — Kara R McMillian
(74) *Attorney, Agent, or Firm* — Kilpatrick Townsend & Stockton LLP

(57) ABSTRACT

Compounds and compositions are provided for treatment, prevention, or amelioration of a variety of medical disorders associated with viral infections and/or cell proliferation. The compounds provided herein are 5-phosphono-pent-2-en-1-yl nucleosides and esters thereof.

18 Claims, No Drawings

U.S. PATENT DOCUMENTS

| | | | |
|---|---|---|---|
| 5,900,252 | A | 5/1999 | Calanchi et al. |
| 5,922,356 | A | 7/1999 | Koseki et al. |
| 5,948,433 | A | 9/1999 | Burton et al. |
| 5,972,366 | A | 10/1999 | Haynes et al. |
| 5,972,891 | A | 10/1999 | Kamei et al. |
| 5,980,945 | A | 11/1999 | Ruiz |
| 5,983,134 | A | 11/1999 | Ostrow |
| 5,985,307 | A | 11/1999 | Hanson et al. |
| 5,985,317 | A | 11/1999 | Venkateshwaran et al. |
| 5,993,855 | A | 11/1999 | Yoshimoto et al. |
| 5,994,321 | A * | 11/1999 | Lewis et al. ............ 514/45 |
| 6,004,534 | A | 12/1999 | Langer et al. |
| 6,010,715 | A | 1/2000 | Wick et al. |
| 6,024,975 | A | 2/2000 | D'Angelo et al. |
| 6,039,975 | A | 3/2000 | Shah et al. |
| 6,045,830 | A | 4/2000 | Igari et al. |
| 6,048,736 | A | 4/2000 | Kosak |
| 6,060,082 | A | 5/2000 | Chen et al. |
| 6,071,495 | A | 6/2000 | Unger et al. |
| 6,087,324 | A | 7/2000 | Igari et al. |
| 6,113,943 | A | 9/2000 | Okada et al. |
| 6,120,751 | A | 9/2000 | Unger |
| 6,131,570 | A | 10/2000 | Schuster et al. |
| 6,139,865 | A | 10/2000 | Friend et al. |
| 6,167,301 | A | 12/2000 | Flower et al. |
| 6,197,350 | B1 | 3/2001 | Yamagata et al. |
| 6,248,363 | B1 | 6/2001 | Patel et al. |
| 6,253,872 | B1 | 7/2001 | Neumann |
| 6,256,533 | B1 | 7/2001 | Yuzhakov et al. |
| 6,261,595 | B1 | 7/2001 | Stanley et al. |
| 6,264,970 | B1 | 7/2001 | Hata et al. |
| 6,267,981 | B1 | 7/2001 | Okamoto et al. |
| 6,267,983 | B1 | 7/2001 | Fujii et al. |
| 6,271,359 | B1 | 8/2001 | Norris et al. |
| 6,274,552 | B1 | 8/2001 | Tamarkin et al. |
| 6,316,652 | B1 | 11/2001 | Steliou |
| 6,376,461 | B1 | 4/2002 | Igari et al. |
| 6,419,961 | B1 | 7/2002 | Igari et al. |
| 6,589,548 | B1 | 7/2003 | Oh et al. |
| 6,613,358 | B2 | 9/2003 | Randolph et al. |
| 6,699,500 | B2 | 3/2004 | Okada et al. |
| 6,740,634 | B1 | 5/2004 | Saikawa et al. |
| 6,924,271 | B2 | 8/2005 | Averett et al. |
| 2004/0077587 | A1 | 4/2004 | Sommadossi et al. |
| 2008/0261913 | A1 | 10/2008 | Sommadossi et al. |
| 2008/0286230 | A1 | 11/2008 | Sommadossi et al. |

OTHER PUBLICATIONS

Chan, et al., 2004, "Discovery of thiophene-2-carboxylic acids as potent inhibitors of HCV NS5B polymerase and HCV subgenomic RNA replication. Part 1: Sulfonamindes," *Bioorg. Med. Chem. Lett.* 14:793-796.

Dhanak, et al., 2002, "Identification and Biological Characterization of Heterocyclic Inhibitors of the Hepatitis C Virus RNA-dependent RNA Polymerase," *J. Biol. Chem.* 277:38322-38327.

Di Marco, et al., "Interdomain Communication of Hepatitis C Virus Polymerase Abolished by Small Molecule Inhibitors Bound to a Novel Allosteric Site," 2005, *J. Biol. Chem.* 280:29765-70.

Gu, et al., 2003, "Arresting Initiation of Hepatitis C Virus RNA Synthesis Using Heterocyclic Derivatives," *J. Biol. Chem.* 278:16602-16607.

Holy, Antonin, 2003, "Phosphonomethoxyalkyl Analogs of Nucleotides," *Current Pharmaceutical Design*, 9, 2567-2592.

Horsmans, et al., 2004, "Isatoribine, A Toll-like Receptor 7 Agonist, Significantly Reduced Plasma Viral Load in a Clinical Proff-of-Concept Study in Patients with Chronic Hepatitis C Virus Infection," *Hepatology* 40 (Suppl. 1), 282A.

Lamarre, et al., 2003, "An NS3 protease inhibitor with antiviral effects in humans infected with hepatitis C virus," *Nature*, 426:186-189.

LaPlante, et al., 2004, "Binding Mode Determination of Benzimidazole Inhibitors of the Hepatitis C Virus RNA Polymerase by a Structure and Dynamics Strategy," *Angew Chem, Int. Ed. Engl.* 43:4306-4311.

Lee, et al., 2003, "Molecular basis for the immunostimulatory activity of guanine nucleoside analogs: Activiation of Toll-like receptor 7," *Proc. Natl. Acad. Scie. USA* 100:6646-6651.

Lin, et al., 2005, "In Vitro Studies of Cross-resistance Mutations against Two Hepatitis C Virus Serine Protease Inhibitors, VX-950 and BILN 2061," *J. Biol. Chem.* Manuscript M506462200 (epublication).

Love, et al., 2003, "Crystallographic Identification of a Noncompetitive Inhibitor Binding Site on the Hepatitis C Virus NS5B RNA Polymerase Enzyme," *J. Virol.* 77:7575-7581.

Maloisel, et al., "Neoglycolipid conjugates of foscarnet with enhanced antiviral activity in cells infected with human cytomegalovirus and herpes simplex virus type 1," *Antiviral Chemistry & Chemotherapy*, 10:333-345.

Nave et al., 1996, Synthesis, enzymatic phosphorylation and antiviral activity of acyclic dienyl phosphonate derivatives of guanine, Bio. & Med. Chemistry Letts., vol. 6, No. 2, pp. 179-184.

Nguyen et al., 2003, "Resistance Profile of a Hepatitis C Virus RNA-Dependant RNA Polymerase Benzothiadiazine Inhibitor," *Antimicrob. Agents Chemother.* 47:3525-3530.

Olsen, et al., 2004, "A 7-Deaza-Adenosine Analog is a Potent and Selective Inhibitor of Hepatitis C Virus Replication with Excellent Pharmacokinetic Properties," *Antimibrob. Agents Chemother.* 48:3944-3953.

Otmar, et al., 1999, "An alternative Synthesis of HPMPC and HPMPA Diphosphoryl Derivatives," *Collection Symposium Series*, vol. 2, 252-254.

Prakash, et al., 2005, "Synthesis and Evaluation of S-Acyl-2-thioethyl Esters of Modified Nucleoside 5'-Monophosphates as Inhibitors of Hepatitis C Virus RNA Replication," *J. Med. Chem.*, 48, 1199-1210.

Randall, et al., 2003, "Clearance of replicating hepatitis C virus replicon RNSa in cell culture by small interfering RNAs," *Proc. Nat'l. Acad. Sci. USA* 100:235-240.

Saudek, et al., 1989, "A Preliminary Trial of the Programmable Implantable Medication System for Insulin Delivery," *N. Engl. J. Med.* 321:574.

Schetter & Vollmer, 2004, "Toll-like receptors involved in the response to microbial pathogens: Development of agonists for toll-like receptor 9," *Curr. Opin. Drug Discov. Dev.* 7:204-210.

Sefton, 1987, "Implantable Pumps," *CRC Crit. Ref. Biomed. Eng.* 14:201.

Summa, Vincenzo, 2005, "VX-950," *Current Opinion in Investigationsal Drugs*, 6 (8):831-837.

Takeda, et al., 2003, "Toll-Like Receptors," *Annu. Rev. Immunol.* 21:335-376.

Tomei, et al., 2004, "Characterization of the Inhibition of Hepatitis C Virus RNA Replication by Nonnucleosides," *J. Virol.* 78:938-946.

Tomei, et al., 2003, "Mechanism of Action and Antiviral Activity of Benzimidazole-Based Allosteric Inhibitors of the Hepatitis C Virus RNA-Dependent RNA Polymerase," *J. Virol.* 77:13225-13231.

Wang, et al., 2003, "Non-nucleoside Analogue Inhibitors Bind to an Allosteric Site on HCV NS5B Polymerase," *J. Biol. Chem.* 278:9489-9495.

Whitby, et al., 2004, "Action of celgosivir (6 O-butanoyl castanospermine) against the pestivirus BVDV: implications for the treatment of hepatitis C," *Antivir. Chem. Chemother.* 15(3):141-51.

* cited by examiner

PHOSPHONO-PENT-2-EN-1-YL NUCLEOSIDES AND ANALOGS

RELATED APPLICATION DATA

This application is a §371 of PCT/US2006/012117, filed March 30, 2006., which claims priority under 35 U.S.C. §119(e) to U.S. provisional application Ser. No. 60/667,740, entitled "Phosphono-Pent-2-En-1-yl Nucleosides And Analogs" to Hostetler et al., filed April 1, 2005. The contents of the provisional application are incorporated by reference herein in their entirety.

GRANT INFORMATION

This invention was made with government support under Grant No. 5R37AI29164 awarded by the National Institute of Allergy and Infectious Diseases/National Health Institute. The United States government has certain rights in this invention.

FIELD

Provided herein are 5-phosphono-pent-2-en-1-yl nucleosides and esters thereof. In one embodiment, the compounds are monoesters of biologically active nucleotides and analogs thereof. In another embodiment, provided herein are methods of treatment, prevention, or amelioration of a variety of medical disorders associated with viral infections and cell proliferation using the compounds and compositions provided herein.

BACKGROUND

Nucleoside phosphonates have long been known to have antiviral, antiproliferative and a variety of other therapeutic benefits. Among these are the antiviral nucleoside phosphonates, such as, for example, cidofovir, cyclic cidofovir, adefovir, tenofovir, and the like, as well as the 5'-phosphonates and methylene phosphonates of azidothymidine (AZT), ganciclovir, acyclovir, and the like. In these compounds, the 5'-hydroxyl of the sugar moiety, or its equivalent in acyclic nucleosides (ganciclovir, penciclovir, acyclovir) which do not contain a complete sugar moiety, is replaced with a phosphorus-carbon bond. In the case of the methylene phosphonates, a methylene group replaces the 5'-hydroxyl or its equivalent, and its carbon atom is, in turn, covalently linked to the phosphonate.

Such compounds may be active as antiviral or antiproliferative nucleotides. Upon cellular metabolism, two additional phosphorylations occur to form the nucleoside phosphonate diphosphate which represents the equivalent of nucleoside triphosphates. Antiviral nucleoside phosphonate diphosphates are selective inhibitors of viral RNA or DNA polymerases or reverse transcriptases. That is to say, their inhibitory action on viral polymerases is much greater than their degree of inhibition of mammalian cell DNA polymerases α, β and γ or mammalian RNA polymerases. Conversely, the antiproliferative nucleoside phosphonate diphosphates inhibit cancer cell DNA and RNA polymerases and may show much lower selectivity versus normal cellular DNA and RNA polymerases.

There is a continuing need for less toxic, more effective pharmaceutical agents to treat a variety of disorders associated with viral infection, and cell proliferation.

SUMMARY

Provided herein are 5-phosphono-pent-2-en-1-yl nucleosides and lipophilic esters thereof. Also provided are compositions and methods of using the compounds and compositions for the treatment of various diseases. In one embodiment, compounds and compositions provided herein have antiviral activity. In another embodiment, provided herein are compounds and compositions that are useful in the treatment, prevention, or amelioration of one or more symptoms associated with cell proliferation.

In certain embodiments, the compounds are 5-phosphono-pent-2-en-1-yl nucleosides and pharmaceutically acceptable derivatives thereof. In other embodiments, the compounds are lipophilic esters of 5-phosphono-pent-2-en. 1-yl nucleosides.

In one embodiment, the compounds for use in the compositions and methods provided herein have formula IA or IB:

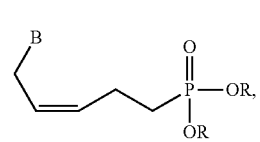

Formula IA

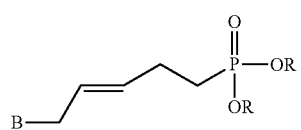

Formula IB or a pharmaceutically active derivative thereof, wherein R is hydrogen, a monovalent cation or a lipophilic group and B is a purine or pyrimidine base or an analog thereof.

Also provided are pharmaceutically-acceptable derivatives, including salts, esters, enol ethers, enol esters, solvates, hydrates and prodrugs of the compounds described herein. Further provided are pharmaceutical compositions containing the compounds provided herein and a pharmaceutically acceptable carrier. In one embodiment, the pharmaceutical compositions are formulated for single dosage administration.

Methods of treating, using the compounds and compositions provided herein are provided. Methods of treating, preventing, or ameliorating one or more symptoms of diseases associated with viral infections and cell proliferation using the compounds and compositions provided herein are provided. In practicing the methods, effective amounts of the compounds or compositions containing therapeutically effective concentrations of the compounds are administered.

Articles of manufacture are provided containing packaging material, a compound or composition provided herein which is useful for treating, preventing, or ameliorating one or more symptoms of diseases or disorders associated with viral infections or cell proliferation using the compounds and compositions provided herein, and a label that indicates that the compound or composition is useful for treating, preventing, or ameliorating one or more symptoms of diseases or disorders associated with viral infections or cell proliferation.

DETAILED DESCRIPTION

A. Definitions

Unless defined otherwise, all technical and scientific terms used herein have the same meaning as is commonly understood by one of ordinary skill in the art to which this invention belongs. All patents, applications, published applications and other publications are incorporated by reference in their entirety. In the event that there are a plurality of definitions for a term herein, those in this section prevail unless stated otherwise.

As used herein, the term "nucleoside base" refers to natural and non-natural purine and pyrimidine bases, including adenine, thymine, cytosine, guanine and uracil and analogs thereof.

Where the nucleoside base contains 1 or more functional groups that may be reactive to form undesired products under the reaction conditions used for preparing the compounds provided herein, for example, the amino groups of cytosine and adenine and the 2-amino and 6-oxo groups of guanine, such functional groups may be blocked using the protecting groups commonly employed in nucleoside chemistry. For example, the amino group of adenine and cytosine may be protected by benzoyl; the 6-oxo and 2-amino groups of guanine may be protected by the triphenylmethyl (trityl) group. The selection of methods for introducing and subsequent removal of such protecting groups are well known to one of ordinary skill in the pertinent art.

As used herein, the terms "lipophilic" or "long-chain" refer to the cyclic, branched or straight chain chemical groups that when covalently linked to a phosphonic acid to form a phosphonate monoester, increase oral bioavailability and enhance activity of the nucleoside phosphonates as compared with the parent nucleoside phosphonates. These lipophilic groups include, but are not limited to alkyl, alkoxyalkyl, and alkylglyceryl. In one embodiment, the alkyl groups contain from 8-26 carbon atoms or 8, 10, 12, 13, 14, 15, 16, 17, 18, 19, 20, 21, 22, 23 or 24 carbon atoms and can be straight or branched chain moieties.

The terms "nucleoside phosphonate" and "acyclic nucleoside phosphonate" refer to the group of phosphonomethoxyalkyl or phosphono substituted nucleoside derivatives that are biologically active, for example, as antiviral, anti-cancer or anti-parasitic drugs.

As used herein, the term "lipophilic monoesters of nucleoside phosphonates" refers to a compound where a lipophilic group is covalently attached to a nucleoside phosphonate via an ester linkage.

As used herein, pharmaceutically acceptable derivatives of a compound include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, nitrates, borates, methanesulfonates, benzenesulfonates, toluenesulfonates, salts of mineral acids, such as but not limited to hydrochlorides, hydrobromides, hydroiodides and sulfates; and salts of organic acids, such as but not limited to acetates, trifluoroacetates, maleates, oxalates, lactates, malates, tartrates, citrates, benzoates, salicylates, ascorbates, succinates, butyrates, valerates and fumarates. Pharmaceutically acceptable esters include, but are not limited to, alkyl, alkenyl, alkynyl, and cycloalkyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is hydrogen, alkyl, alkenyl, alkynyl, and cycloalkyl. Pharmaceutically acceptable enol esters include, but are not limited to, derivatives of formula C=C(OC(O)R) where R is hydrogen, alkyl, alkenyl, alkynyl, or cycloalkyl. Pharmaceutically acceptable solvates and hydrates are complexes of a compound with one or more solvent or water molecules, or 1 to about 100, or 1 to about 10, or one to about 2, 3 or 4, solvent or water molecules.

As used herein, treatment means any manner in which one or more of the symptoms of a disease or disorder are ameliorated or otherwise beneficially altered. Treatment also encompasses any pharmaceutical use of the compositions herein, such as use for treating viral infections and cell proliferative diseases or disorders.

As used herein, amelioration of the symptoms of a particular disorder by administration of a particular compound or pharmaceutical composition refers to any lessening, whether permanent or temporary, lasting or transient that can be attributed to or associated with administration of the composition.

As used herein, $EC_{50}$ refers to a dosage, concentration or amount of a particular test compound that elicits a dose-dependent response at 50% of maximal expression of a particular response that is induced, provoked or potentiated by the particular test compound.

As used herein, a prodrug is a compound that, upon in vivo administration, is metabolized by one or more steps or processes or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392). Other prodrugs for use herein are described elsewhere herein.

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures. It is understood that the compounds provided herein encompass any racemic, optically active, polymorphic, or stereoisomeric form, or mixtures thereof, of a compound of the invention, which possesses the useful properties described herein, it being well known in the art how to prepare optically active forms and how to determine antiproliferative activity using the standard tests described herein, or using other similar tests which are well known in the art. Examples of methods that can be used to obtain optical isomers of the compounds provided herein include the following:

i) physical separation of crystals—a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization—a technique whereby the individual enantiomers are separately crystallized from a solution of the racemate, possible only if the latter is a conglomerate in the solid state;

iii) enzymatic resolutions—a technique whereby partial or complete separation of a racemate by virtue of differing rates of reaction for the enantiomers with an enzyme iv) enzymatic asymmetric synthesis—a synthetic technique whereby at least one step of the synthetic steps uses an enzymatic reaction to obtain an enantiomerically pure or enriched synthetic precursor of the desired enantiomer;

v) chemical asymmetric synthesis—a synthetic technique whereby the desired enantiomer is synthesized from an achiral precursor under conditions that produce asymmetry (i.e., chirality) in the product, which may be achieved using chiral catalysts or chiral auxiliaries;

vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the enantiomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography—a technique whereby the racemate is volatilized and enantiomers are separated by virtue of their differing interactions in the gaseous mobile phase with a column containing a fixed non-racemic chiral adsorbent phase;

xii) extraction with chiral solvents—a technique whereby the enantiomers are separated by virtue of preferential dissolution of one enantiomer into a particular chiral solvent;

xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

As used herein, substantially pure means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

As used herein, the term "alkyl" refers to a monovalent straight or branched chain or cyclic radical. In certain embodiments, the alkyl group contains from one to twenty-four carbon atoms, including methyl, ethyl, n-propyl, isopropyl, n-butyl, isobutyl, tert-butyl, n-hexyl, octadecyl, nonadecyl, eicosyl, 18-methyl-nonadecyl, 19-methyl-eicosyl, and the like. As used herein lower alkyl refers to alkyl groups of 1 to 6 carbon atoms.

As used herein, "substituted alkyl" refers to alkyl groups further bearing one or more substituents, including, but not limited to substituents selected from lower alkyl, hydroxy, alkoxy (of a lower alkyl group), mercapto (of a lower alkyl group), cycloalkyl, substituted cycloalkyl, heterocyclic, substituted heterocyclic, aryl, substituted aryl, heteroaryl, substituted heteroaryl, aryloxy, substituted aryloxy, halogen, trifluoromethyl, cyano, azido, nitro, nitrone, amino, amido, formyl, acyl, oxyacyl, carboxyl, carbamate, sulfonyl, sulfonamide, and sulfuryl, which may be protected or unprotected as necessary, as taught in Greene, et al., Protective Groups in Organic Synthesis, John Wiley and Sons, Second Ed. 1991, hereby incorporated by reference.

As used herein, "alkenyl" refers to straight or branched chain hydrocarbon group having one or more carbon-carbon double bonds. In certain embodiments, the alkenyl group contains from 2 up to 24 carbon atoms, and "substituted alkenyl" refers to alkenyl groups further bearing one or more substituents as set forth above.

As used herein, "alkynyl" refers to straight or branched chain hydrocarbon group having one or more carbon-carbon triple bonds. In certain embodiments, the alkynyl group contains from 2 up to 24 carbon atoms, and "substituted alkynyl" refers to alkynyl groups further bearing one or more substituents as set forth above.

As used herein, "aryl" refers to aromatic groups having in the range of 6 up to 14 carbon atoms and "substituted aryl" refers to aryl groups further bearing one or more substituents as set forth above.

As used herein, "heteroaryl" refers to aromatic groups containing one or more heteroatoms (e.g., N, O, S, or the like) as part of the ring structure, and having in the range of 3 up to 14 carbon atoms and "substituted heteroaryl" refers to heteroaryl groups further bearing one or more substituents as set forth above.

As used herein "subject" is an animal, such as a mammal, including human, such as a patient.

The phrase "effective amount" as used herein means an amount required for prevention, treatment, or amelioration of one or more of the symptoms of diseases or disorders associated including those associated with viral infection, cell proliferation and/or bone metabolism.

Where the number of any given substituent is not specified (e.g., haloalkyl), there may be one or more substituents present. For example, "haloalkyl" may include one or more of the same or different halogens.

As used herein, the term "parenteral" includes subcutaneous, intravenous, intra-arterial, intramuscular or intravitreal injection, or infusion techniques.

The term "topically" encompasses administration rectally and by inhalation spray, as well as the more common routes of the skin and mucous membranes of the mouth and nose and in toothpaste.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:942-944).

Some abbreviations used herein are as follows:
5-Phosphono-pent-2-en-1-yl adenine=PPen-A,
5-Phosphono-pent-2-en-1-yl cytosine=PPen-C,
5-Phosphono-pent-2-en-1-yl guanine=PPen-G,
5-Phosphono-pent-2-en-1-yl thymine=PPen-T and
5-Phosphono-pent-2-en-1-yl uracil=PPen-U,
Hexadecyloxypropyl=HDP
Octadecyloxyethyl=ODE
Oleyloxyethyl=OLE, and
Oleyloxypropyl=OLP.

B. Compounds

In certain embodiments provided herein are 5-phosphono-pent-2-en-1-yl nucleosides and lipophilic esters thereof. In one embodiment, the compounds for use in the compositions and methods provided herein have formula IIA or IIB:

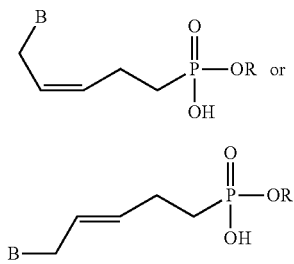

Formula IIA

Formula IIB or pharmaceutically active derivatives thereof, wherein R is hydrogen, a monovalent cation or a lipophilic group and B is a purine or pyrimidine base or an analog thereof.

In certain embodiments, R is hydrogen, a monovalent cation, a substituted or unsubstituted $C_8$-$C_{24}$ alkyl or substituted or unsubstituted $C_8$-$C_{24}$ alkenyl having from 1 to 6 double bonds, wherein substituents when present are selected from one or more, in one embodiment, one to four, in another embodiment, one, two or three halogen, alkyl, —OH, —SH, cycloalkyl and epoxide; or R is acetyl, valyl, dipivoxil, bis (pivaloyloxymethyl) or disoproxil. In certain embodiments, R has formula:

In certain embodiments, R has formula:

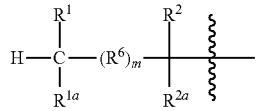

wherein:
$R^1$ and $R^{1a}$ are each independently —H, —O($C_1$-$C_{24}$)alkyl, —O($C_1$-$C_{24}$)alkenyl, —O($C_1$-$C_{24}$)acyl, —S($C_1$-$C_{24}$)alkyl, —S($C_1$-$C_{24}$)alkenyl, or —S($C_1$-$C_{24}$)acyl, wherein at least one of $R^1$ and $R^{1a}$ is not —H, and wherein the alkenyl or acyl moieties optionally have 1 to 6 double bonds, $R^2$ and $R^{2a}$ are each independently —H, —O($C_1$-$C_7$)alkyl, —O($C_1$-$C_7$)alkenyl, —S($C_1$-$C_7$)alkyl, —S($C_1$-$C_7$)alkenyl, —O($C_1$-$C_7$)acyl, —S($C_1$-$C_7$)acyl, —N($C_1$-$C_7$)acyl, —NH ($C_1$-$C_7$)alkyl, —N(($C_1$-$C_7$)alkyl)$_2$, oxo, halogen, —NH$_2$, —OH, or —SH;

$R^6$, when present, is:

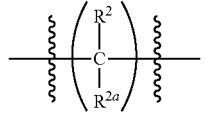

m is an integer from 0 to 6;
and wherein $R^1$, $R_{1a}$, $R^2$, $R^{2a}$, $R^7$ and $R^{7a}$ are optionally substituted with one to four substituents, in one embodiment, one, two or three substituents, each independently selected from alkyl, alkenyl, alkynyl, halo, hydroxyl, pseudohalo, amino, nitro, cycloalkyl, heterocyclyl, aryl and heteroaryl.

In certain embodiments, m=0, 1 or 2. In certain embodiments, m=0 or 1. In certain embodiments, m=0. In certain embodiments, m=1. In certain embodiments, $R^2$ and $R^{2a}$ are H.

In one embodiment, the alkyl, alkenyl and alkynyl groups in the compounds provided herein are substituted with one or more, in one embodiment, one, two, three or four substituents selected from alkyl, alkenyl, alkynyl, halo, hydroxyl, pseudohalo, amino, nitro, cycloalkyl, heterocyclyl, aryl and heteroaryl.

In certain embodiments, R has formula:

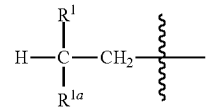

wherein $R^1$ and $R^{1a}$, are as defined elsewhere herein.
In one embodiment. R has formula:

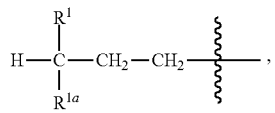

wherein $R^1$ and $R^{1a}$, are as defined elsewhere herein.
In certain embodiments, R has formula:

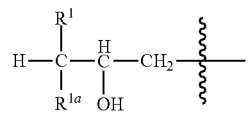

wherein $R^1$ and $R^{1a}$, are as defined elsewhere herein.
In certain embodiments, R is acetyl, valyl, dipivoxil, bis (pivaloyloxymethyl) or disoproxil. Optionally, both —OH moieties of the phosphonate may be substituted by the foregoing substituents.

In one embodiment, R is hexadecyloxypropyl, octadecyloxyethyl, or oleyloxyethyl.

In certain embodiments, $R^1$ is an alkoxy group having the formula —O—$(CH_2)_t$—$CH_3$ wherein t is 0-24. In other embodiments, t is 8, 10, 12, 13, 14, 15, 16, 17, 18, 19 or 20. In other embodiments, t is 13, 14, 15, 16, 17, 18, 19 or 20. In other embodiments, t is 15, 16, 17, 18, 19 or 20. In other embodiments, t is 17, 18, 19 or 20. In other embodiments, t is 15 or 17.

In some embodiments, R is a substituted or unsubstituted $C_8$-$C_{24}$ alkyl, substituted or unsubstituted $C_8$-$C_{24}$ alkenyl having from 1 to 6 double bonds or substituted or unsubstituted $C_8$-$C_{24}$ alkynyl having from 1 to 6 triple bonds, wherein substituents when present are selected from one or more, in one embodiment, one to four, in another embodiment, one, two or three halogen, alkyl, —OR$^w$, —SR$^w$, cycloalkyl or epoxide, where R$^w$ is hydrogen or alkyl and where the alkyl, alkenyl, alkynyl groups may be further substituted or unsubstituted.

In certain embodiments, R is selected from alkyl, alkenyl and alkynyl groups that contain 8, 10, 12, 13, 14, 15, 16, 17, 18, 19, 20, 21, 22, 23 or 24 carbon atoms and can be straight or branched chain moieties. In certain embodiments, the R group is a $C_{16}$-$C_{23}$ straight or branched chain alkyl or $C_{16}$-$C_{23}$ straight or branched chain alkenyl. In other embodiments, R is a $C_{17}$-$C_{19}$ straight or branched chain alkyl or $C_{17}$-$C_{19}$ straight or branched chain alkenyl. In other embodiments, R is $C_{17}$-alkyl, $C_{18}$-alkyl or $C_{19}$ alkyl. In other embodiments, R is $C_{17}$-alkenyl, $C_{18}$-alkenyl or $C_{19}$ alkenyl. In other embodiments, R is $C_{17}$-$C_{22}$ alkyl. In other embodiments, R is $C_{17}$ alkyl, $C_{18}$ alkyl, $C_{19}$ alkyl, $C_{20}$ alkyl, $C_{21}$ alkyl, or $C_{22}$ alkyl.

In other embodiments, R is $C_{16}$-$C_{23}$ alkyl that is substituted with one or more, in one embodiment, one to four, in another embodiment, one, two or three groups selected from lower alkyl and halo. In certain embodiments, R is substituted with one or more, in one embodiment, one to four, in another embodiment, one, two or three methyl groups. In certain embodiments, R is substituted with one or more, in one embodiment, one to four, in another embodiment, one, two or three fluoro groups. In certain embodiments, R is $C_{16}$-$C_{23}$ alkyl and is substituted with one or more, in one embodiment, one to four, in another embodiment, one, two or three methyl or fluoro groups. In certain embodiments, the methyl group or the fluoro group substituent is present on the penultimate carbon of the alkyl, alkenyl, or alkynyl chain. In certain embodiments, R is 7-methyl-octyl, 8-methyl-nonyl, 9-methyl-decyl, 10-methyl-undecyl, 11-methyl-dodecyl, 12-methyl-tridecyl, 13-methyl-tetradecyl, 14-methyl-pentadecyl, 15-methyl-hexadecyl, 16-methyl-heptadecyl, 17-methyl-octadecyl, 18-methyl-nonadecyl, 19-methyl-eicosyl, 20-methyl-heneicosyl, 21-methyl-docosyl, 22-methyl-tricosyl, 7-fluoro-octyl, 8-fluoro-nonyl, 9-fluoro-decyl, 10-fluoro-undecyl, 11-fluoro-dodecyl, 12-fluoro-tridecyl, 13-fluoro-tetradecyl, 14-fluoro-pentadecyl, 15-fluoro-hexadecyl, 16-fluoro-heptadecyl, 17-fluoro-octadecyl, 18-fluoro-nonadecyl, 19-fluoro-eicosyl, 20-fluoro-heneicosyl, 21-fluoro-docosyl or 22-fluoro-tricosyl.

In certain embodiments, B is selected from a natural or non natural purine or pyrimidine base. In certain embodiments, the B is

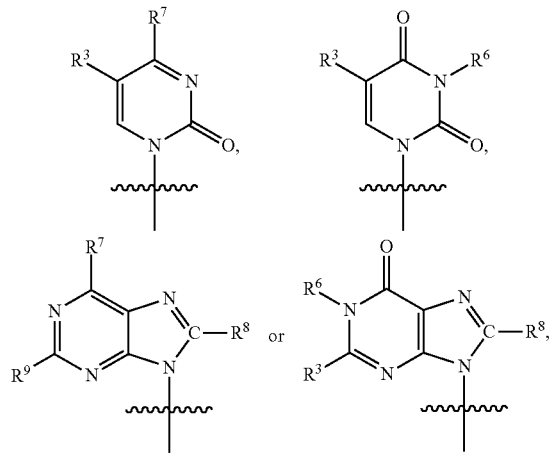

wherein R$^3$ is H, $C_{1-6}$ alkyl, $C_{2-6}$ alkenyl, $C_{2-6}$ alkynyl, $C_{3-6}$ cycloalkyl, hydroxy, halo, aryl or heteroaryl;

R$^6$ is H or $C_{1-6}$ alkyl, $C_{2-6}$ alkenyl, $C_{2-6}$ alkynyl or cycloalkyl;

R$^7$ is H, hydroxy, halo, $C_{1-6}$ alkyl, $C_{2-6}$ alkenyl, $C_{2-6}$ alkynyl, cycloalkyl or NR$^4$R$^5$;

R$^8$ is H, $C_{1-6}$ alkyl, $C_{2-6}$ alkenyl, $C_{2-6}$ alkynyl or cycloalkyl and R$^9$ is H, $C_{1-6}$ alkyl, $C_{2-6}$ alkenyl, $C_{2-6}$ alkynyl, cycloalkyl, halo or NR$^4$R$^5$, where R$^4$ and R$^5$ are each independently H, $C_{1-6}$ alkyl, $C_{2-6}$ alkenyl, $C_{2-6}$ alkynyl, or $C_{3-6}$ cycloalkyl.

In other embodiments, R$^3$ is H, $C_{1-6}$ alkyl, $C_{2-6}$ alkenyl, $C_{2-6}$ alkynyl, $C_{3-6}$ cycloalkyl, hydroxy, halo, aryl or heteroaryl. In some embodiments, R$^3$ is H or $C_{1-6}$ alkyl. In one embodiment, R$^3$ is H. In another embodiment, R$^3$ is methyl.

In another embodiment, R$^4$ and R$^5$ are each independently H, $C_{1-6}$ alkyl, $C_{2-6}$ alkenyl, $C_{2-6}$ alkynyl, or $C_{3-6}$ cycloalkyl. In other embodiments, R$^4$ is H, $C_{1-6}$ alkyl or $C_{3-6}$ cycloalkyl. In one embodiment, R$^4$ is H, methyl or cyclopropyl. In other embodiments, R$^5$ is H, $C_{1-6}$ alkyl or $C_{3-6}$ cycloalkyl. In one embodiment, R$^5$ is H, methyl or cyclopropyl.

In some embodiments, R$^6$ is H or $C_{1-6}$ alkyl, $C_{2-6}$ alkenyl, $C_{2-6}$ alkynyl or cycloalkyl. In other embodiments, R$^6$ is H or $C_{1-6}$ alkyl. In one embodiment, R$^6$ is H or methyl. In another embodiment, R$^6$ is H. In another embodiment, R$^6$ is methyl.

In some embodiments, R$^7$ is H, hydroxy, halo, $C_{1-6}$ alkyl, $C_{2-6}$ alkenyl, $C_{2-6}$ alkynyl, cycloalkyl or NR$^4$R$^5$. In other embodiments, R$^7$ is H, $C_{1-6}$ alkyl, or NR$^4$R$^5$. In one embodiment, R$^7$ is methyl. In another embodiment, R$^7$NR$^4$R$^5$. In other embodiment, R$^7$ is NH$_2$.

In some embodiments, R$^8$ is H, $C_{1-6}$ alkyl, $C_{2-6}$ alkenyl, $C_{2-6}$ alkynyl or cycloalkyl. In one embodiment, R$^8$ is H.

In some embodiments, R$^9$ is H, $C_{1-6}$ alkyl, $C_{2-6}$ alkenyl, $C_{2-6}$ alkynyl, cycloalkyl, halo or NR$^4$R$^5$. In other embodiments, R$^9$ is H.

In other embodiments, B is selected from pyrimidin-1-yl, pyrimidin-3-yl, purin-3-yl, purin-7-yl and purin-9-yl residue. In certain embodiments, B is thymin-1-yl, cytosine-1-yl, adenine-9-yl or guanine-9-yl.

In one embodiment, B is selected from:

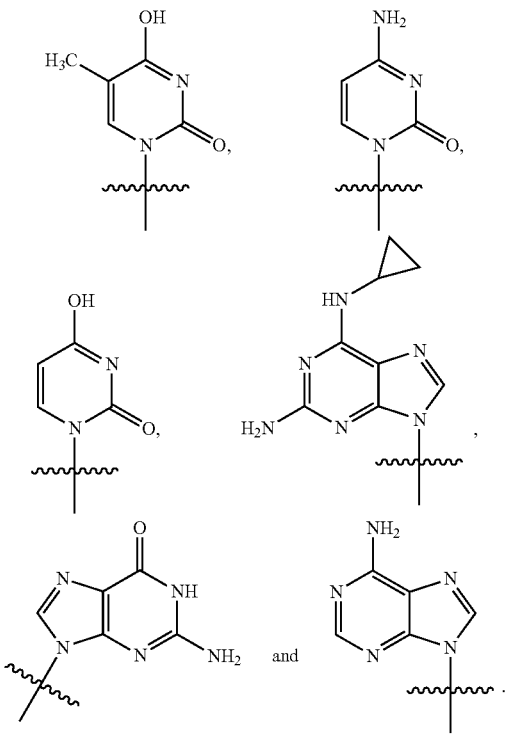

In another embodiment, the compounds herein are selected from
5-phosphono-pent-2-en-1-yl adenine (PPen-A), 5-phosphono-pent-2-en-1-yl cytosine (PPen-C), 5-phosphono-pent-2-en-1-yl guanine (PPen-G), 5-5 phosphono-pent-2-en-1-yl thymine (PPen-T) and 5-phosphono-pent-2-en-1-yl uracil (PPen-U) and lipophilic esters thereof. In some embodiments, the lipophilic esters are hexadecyloxypropyl (HDP) esters, octadecyloxyethyl (ODE) esters and oleyloxyethyl (OLE) esters. In certain embodiments, the compound is selected from:

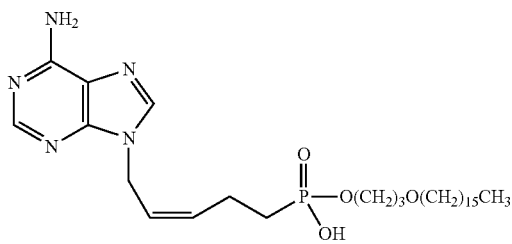

(Z)-3-hexadecyloxy)propyl hydrogen 5-(6-amino-9H-purin-9-yl)pent-3-enylphosphonate or HDP-PPen-A

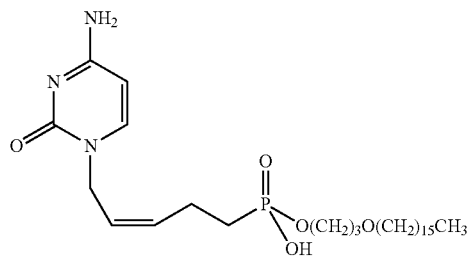

(3Z)-3-(hexadecyloxy)propyl hydrogen 5-(4-amino-2-oxopyrimidin-1(2H)-yl)pent-3-enylphosphonate or HDP-Ppen-C

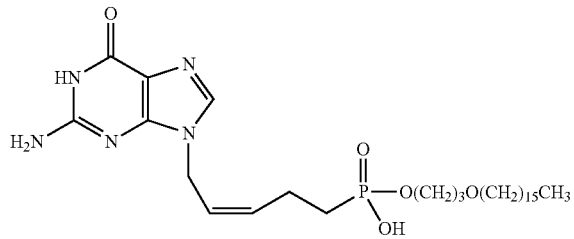

(Z)-3-(hexadecyloxy)propyl hydrogen 5-(2-amino-6-oxo-1,6-dihydropurin-9-yl)pent-3-enylphosphonate or HDP-PPen-G

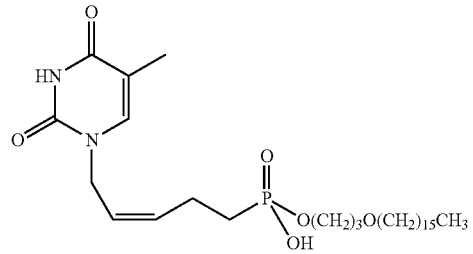

(3Z)-3-(hexadecyloxy)propyl hydrogen 5-3,4-dihydro-5-methyl-2,4-dioxopyrimidin-1(2H)-yl)pent-3-enylphosphonate or HDP-Ppen-T

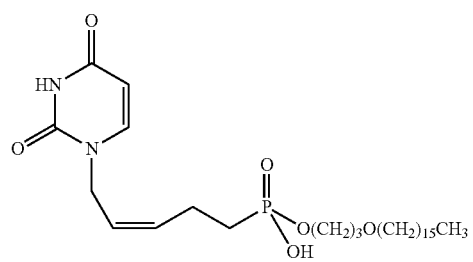

(3Z)-3-(hexadecyloxy)propyl hydrogen 5-(3,4-dihydro-2,4-dioxopyrimidin-1(2H)-yl)pent-3-enylphosphonate or HDP-PPen-U

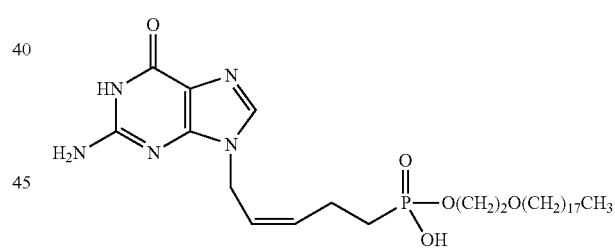

(Z)-2-(octadecyloxy)ethyl hydrogen 5-(2-amino-6-oxo-1,6-dihydropurin-9-yl)pent-3-enylphosphonate or ODE-PPen-G, and

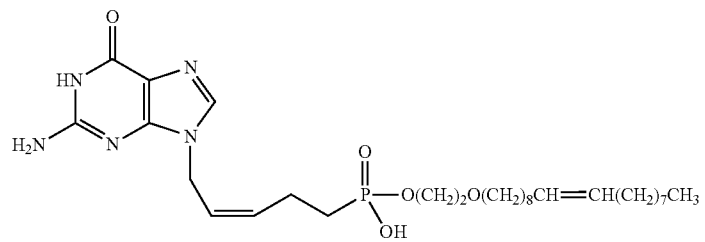

(Z)-2-(octadec-9-enyloxy)ethyl hydrogen 5-(2-amino-6-oxo-1,6-dihydropurin-9-yl)pent-3-enylphosphonate 5 or OLE-PPen-G

C. Preparation of the Compounds

Exemplary methods for the 5-phosphono-pent-2-en-1-yl nucleosides and esters thereof for use in the compositions and methods provided herein are described below and in Examples but other methods known in the art can be used to prepare the 5-phosphono-pent-2-en-1-yl nucleosides and esters thereof provided herein.

Scheme I outlines the synthesis of the key intermediate 9. Example 1 provides conditions for the synthesis of compound 9. In this process, 3-buten-1-ol 1 is treated with DHP and PPTS to give compound 2. Hydroxymethylation of compound 2 provides compound 3, which is protected with TBDPSCl to give compound 5. Compound 5 is converted to the phosphonate compound 7 through bromination and Arbuzov reaction. After partial hydrogenation of compound 7, deprotection of TBDPS group provides the key intermediate 9.

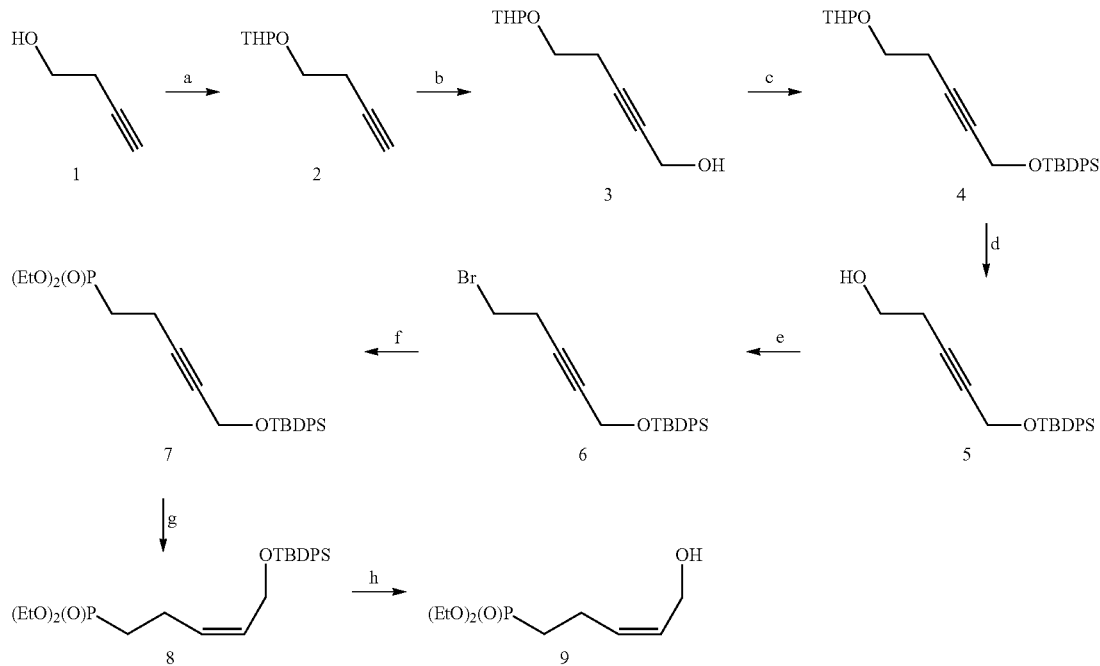

Scheme I

Reagents and conditions: a) DHP, PPTS, $CH_2Cl_2$, rt, b) n-BuLi, $(CH_2O)_n$, −78° C., c) TBDPSCl, imidazole, $CH_2Cl_2$, rt, d) MeOH PPTS, rt, e) $CBr_4$, $PPh_3$, $CH_2Cl_2$, −78° C., f) $P(OEt)_3$, reflux, g) $H_2$, Lindlar's catalyst, MeOH, rt, h) TBAF, acetonitrile, 0° C.

Scheme Ia outlines the synthesis of the key intermediate 9a required in the synthesis of E isomers of formula IB. Intermediate 7 can be prepared using similar steps as described above in Scheme I. Intermediate 7 is hydrogenated in presence of alkali metals (Li or Na) in liquid ammonia or ethylamine at low temperatures to obtain intermediate 8a which is deprotected to yield intermediate 9a.

Scheme Ia

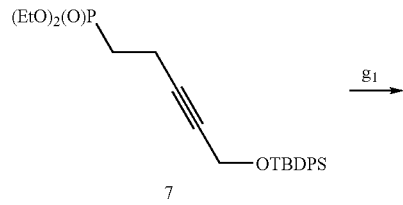

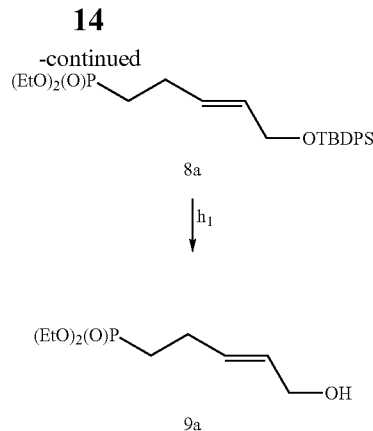

Scheme II illustrates the synthesis of the compounds provided herein using the key intermediate 9. Synthesis of PPen-A is described in detail in example 2. The key intermediate 9 undergoes Mitsunobu reaction with adenine to give compound 10, which is hydrolyzed under acidic conditions to give PPen-A (13). In example 3, synthesis of PPen-G (15) is described. Mitsunobu reaction with 2-amino-6-chloropurine provides compound 11, of which the nucleobase is converted to the guanine to give compound 12. The compound 12 is hydrolyzed using TMSBr to give PPen-G (15). In example 4, PPen-A is converted to its corresponding monophosphonoester, HDP-PPen-A. In example 5, compound 11 is converted to HDP-PPen-G. Compound 11 is hydrolyzed under acidic conditions to give compound 14, which undergoes DCC coupling with 3-hexadecyloxy-propan-1-ol (HDP-OH) to afford compound 17. Compound 17 is treated with 88% HCOOH under reflux conditions to give HDP-PPen-G (18).

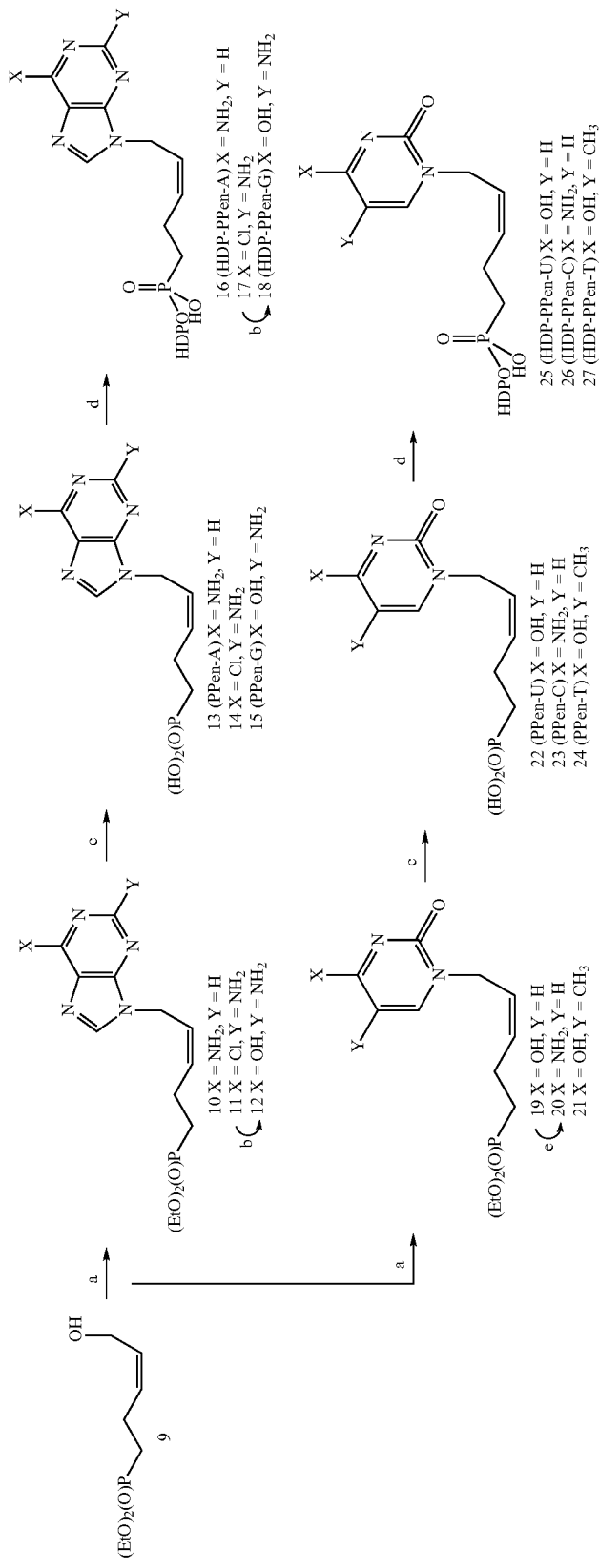

Reagents and conditions: a) DIAD, PPh$_3$, nucleobases, DMF, 0° C. or rt b) HCOOH, reflux, c) TMSBr, acetonitrile, rt, d) HDP-OH, DCC, DMAP, DMF, 60° C., e) i) 2,4,6-triisopropylbenzenesulfonyl chloride, TEA, DMAP, acetonitril, rt, ii) NH$_4$OH D. Formulation of Pharmaceutical Compositions The pharmaceutical compositions provided herein contain therapeutically effective amounts of one or more of the compounds provided herein that are useful in the prevention, treatment, or amelioration of one or more of the symptoms of diseases or disorders associated with viral infections and inappropriate cell proliferation and a pharmaceutically acceptable carrier. Pharmaceutical carriers suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients.

The compositions contain one or more compounds provided herein. The compounds are, in one embodiment, formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. In one embodiment, the compounds described above are formulated into pharmaceutical compositions using techniques and procedures well known in the art ((see, e.g., Ansel Introduction to Pharmaceutical Dosage Forms, Seventh Edition 1999).

In the compositions, effective concentrations of one or more compounds or pharmaceutically acceptable derivatives thereof is (are) mixed with a suitable pharmaceutical carrier. The compounds may be derivatized as the corresponding salts, esters, enol ethers or esters, acetals, ketals, orthoesters, hemiacetals, hemiketals, acids, bases, solvates, hydrates or prodrugs prior to formulation, as described above. The concentrations of the compounds in the compositions are effective for delivery of an amount, upon administration, that treats, prevents, or ameliorates one or more of the symptoms of diseases or disorders associated with associated with viral infections or inappropriate cell proliferation. In one embodiment, the compositions are formulated for single dosage administration. To formulate a composition, the weight fraction of a compound is dissolved, suspended, dispersed or otherwise mixed in a selected carrier at an effective concentration such that the treated condition is relieved, prevented, or one or more symptoms are ameliorated.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems well known to those of skill in the art and then extrapolated therefrom for dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of diseases or disorders associated with viral infections or inappropriate cell proliferation, as described herein.

In one embodiment, a therapeutically effective dosage should produce a serum concentration of active ingredient of from about 0.1 ng/ml to about 50-100 μg/ml. The pharmaceutical compositions, in another embodiment, should provide a dosage of from about 0.001 mg to about 2000 mg of compound per kilogram of body weight per day. Pharmaceutical dosage unit forms are prepared to provide from about 0.01 mg, 0.1 mg or 1 mg to about 500 mg, 1000 mg or 2000 mg, and in one embodiment from about 10 mg to about 500 mg of the active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate. Derivatives of the compounds, such as prodrugs of the compounds may also be used in formulating effective pharmaceutical compositions.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are, in one embodiment, formulated and administered in unit-dosage forms or multiple-dosage forms. Unit-dose forms as used herein refer to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, and other such agents.

Actual methods of preparing such dosage forms are known, or will be apparent, to those skilled in this art; for example, see Remington's Pharmaceutical Sciences, Mack Publishing Company, Easton, Pa., 15th Edition, 1975.

Dosage forms or compositions containing active ingredient in the range of 0.005% to 100% with the balance made up from non-toxic carrier may be prepared. Methods for preparation of these compositions are known to those skilled in the art. The contemplated compositions may contain 0.001%-100% active ingredient, in one embodiment 0.1-95%, in another embodiment 75-85%.

In certain embodiments, the compositions are lactose-free compositions containing excipients that are well known in the art and are listed, for example, in the U.S. Pharmacopeia (USP) 25-NF20 (2002). In general, lactose-free compositions contains active ingredients, a binder/filler, and a lubricant in pharmaceutically compatible and pharmaceutically acceptable amounts. Particular lactose-free dosage forms contain active ingredients, microcrystalline cellulose, pre-gelatinized starch, and magnesium stearate.

Further provided are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles& Practice*, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms provided herein can be prepared using anhydrous or low moisture containing ingredients and low moisture or low humidity conditions.

An anhydrous pharmaceutical composition should be prepared and stored such that its anhydrous nature is maintained. Accordingly, anhydrous compositions are generally packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

1. Compositions for Oral Administration

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

a. Solid Compositions for Oral Administration

In certain embodiments, the formulations are solid dosage forms, in one embodiment, capsules or tablets. The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an emetic coating; and a film coating. Examples of binders include microcrystalline cellulose, gum tragacanth, glucose solution, acacia mucilage, gelatin solution, molasses, polyinylpyrrolidine, povidone, crospovidones, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

The compound, or pharmaceutically acceptable derivative thereof, could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

b. Liquid Compositions for Oral Administration

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such as fruits, and synthetic blends of compounds which produce a pleasant taste sensation.

For a solid dosage form, the solution or suspension, in for example, propylene carbonate, vegetable oils or triglycerides, is in one embodiment encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. RE28,819 and 4,358,603. Briefly, such formulations include, but are not limited to, those containing a compound provided herein, a dialkylated mono- or poly-alkylene glycol, including, but not limited to, 1,2-dimethoxyethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl)acetals of lower alkyl aldehydes such as acetaldehyde diethyl acetal.

2. Injectables, Solutions and Emulsions

Parenteral administration, in one embodiment characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. In one embodiment, a therapeutically effective dosage is formulated to contain a concentration of at least about 0.1% w/w up to about 90% w/w or more, in certain embodiments more than 1% w/w of the active compound to the treated tissue(s).

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

3. Sustained Release Dosage Form

Active ingredients provided herein can be administered by controlled release means or by delivery devices that are well known to those of ordinary skill in the art. Examples include, but are not limited to, those described in U.S. Pat. Nos. 3,845, 770; 3,916,899; 3,536,809; 3,598,123; and 4,008,719; 5,674, 533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; 6,699,500 and 6,740,634, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients provided herein.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

In certain embodiments, the agent may be administered using intravenous infusion, an implantable osmotic pump, a transdermal patch, liposomes, or other modes of administration. In one embodiment, a pump may be used (see, Sefton, CRC Crit. Ref Biomed Eng. 14:201 (1987); Buchwald et al., Surgery 88:507 (1980); Saudek et al., N. Engl. J. Med. 321: 574 (1989). In another embodiment, polymeric materials can be used. In yet another embodiment, a controlled release system can be placed in proximity of the therapeutic target, i.e., thus requiring only a fraction of the systemic dose (see, e.g., Goodson, Medical Applications of Controlled Release, vol. 2, pp. 115-138 (1984). In some embodiments, a controlled release device is introduced into a subject in proximity of the site of inappropriate immune activation or a tumor. Other controlled release systems are discussed in the review by Langer (Science 249:1527-1533 (1990). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient contained in such parenteral compositions is highly dependent on the specific nature thereof, as well as the needs of the subject.

4. Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, an antioxidant, a buffer and a bulking agent. In some embodiments, the excipient is selected from dextrose, sorbital, fructose, corn syrup, xylitol, glycerin, glucose, sucrose and other suitable agent. The solvent may contain a buffer, such as citrate, sodium or potassium phosphate or other such buffer known to those of skill in the art at, at about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

5. Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will, in one embodiment, have diameters of less than 50 microns, in one embodiment less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

For nasal administration, the preparation may contain an esterified phosphonate compound dissolved or suspended in a liquid carrier, in particular, an aqueous carrier, for aerosol application. The carrier may contain solubilizing agents such as propylene glycol, surfactants, absorption enhancers such as lecithin or cyclodextrin, or preservatives.

These solutions, particularly those intended for ophthalmic use, may be formulated as 0.01%-10% isotonic solutions, pH about 5-7, with appropriate salts.

6. Compositions for Other Routes of Administration

Other routes of administration, such as transdermal patches, including iontophoretic and electrophoretic devices, and rectal administration, are also contemplated herein.

Transdermal patches, including iotophoretic and electrophoretic devices, are well known to those of skill in the art. For example, such patches are disclosed in U.S. Pat. Nos. 6,267,983, 6,261,595, 6,256,533, 6,167,301, 6,024,975, 6,010715, 5,985,317, 5,983,134, 5,948,433, and 5,860,957.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is about 2 to 3 gm. Tablets and capsules for rectal administration are manufactured using the same pharmaceutically acceptable substance and by the same methods as for formulations for oral administration.

7. Targeted Formulations

The compounds provided herein, or pharmaceutically acceptable derivatives thereof, may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In one embodiment, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

8. Articles of Manufacture

The compounds or pharmaceutically acceptable derivatives may be packaged as articles of manufacture containing packaging material, a compound or pharmaceutically acceptable derivative thereof provided herein, which is effective for treatment, prevention or amelioration of one or more symptoms of diseases or disorders associated with viral infections or inappropriate cell proliferation, within the packaging material, and a label that indicates that the compound or composition, or pharmaceutically acceptable derivative thereof, is used for the treatment, prevention or amelioration of one or more symptoms of diseases or disorders associated with viral infections or inappropriate cell proliferation.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease or disorder associated with viral infections or inappropriate cell proliferation.

E. Dosages

In human therapeutics, the physician will determine the dosage regimen that is most appropriate according to a preventive or curative treatment and according to the age, weight, stage of the disease and other factors specific to the subject to be treated. The pharmaceutical compositions, in another embodiment, should provide a dosage of from about 0.001 mg to about 2000 mg of compound per kilogram of body weight per day. Pharmaceutical dosage unit forms are prepared, e.g., to provide from about 0.01 mg, 0.1 mg or 1 mg to about 500 mg, 1000 mg or 2000 mg, and in one embodiment from about 10 mg to about 500 mg of the active ingredient or a combination of essential ingredients per dosage unit form.

The amount of active ingredient in the formulations provided herein, which will be effective in the prevention or treatment of a disorder or one or more symptoms thereof, will vary with the nature and severity of the disease or condition, and the route by which the active ingredient is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject.

Exemplary doses of a formulation include milligram or microgram amounts of the active compound per kilogram of subject or sample weight (e.g., from about 1 micrograms per kilogram to about 50 milligrams per kilogram, from about 10 micrograms per kilogram to about 30 milligrams per kilogram, from about 100 micrograms per kilogram to about 10 milligrams per kilogram, or from about 100 microgram per kilogram to about 5 milligrams per kilogram).

It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the composition provided herein are also encompassed by the above described dosage amounts and dose frequency schedules. Further, when a subject is administered multiple dosages of a composition provided herein, not all of the dosages need be the same. For example, the dosage administered to the subject may be increased to improve the prophylactic or therapeutic effect of the composition or it may be decreased to reduce one or more side effects that a particular subject is experiencing.

In certain embodiments, administration of the same formulation provided herein may be repeated and the administrations may be separated by at least 1 day, 2 days, 3 days, 5 days, 10 days, 15 days, 30 days, 45 days, 2 months, 75 days, 3 months, or 6 months.

F. Evaluation of the Activity of the Compounds

The activity of the compounds as antivirals can be measured in standard assays known in the art. Exemplary assays include, but are not limited to, plaque reduction assay in HFF cells, DNA reduction assay in MRC-5 cells, p24 reduction assay in MT-2 cells, CPE assay in HFF cells and EBV Elisa assay in Daudi cells.

In Table 1, $EC_{50}$ for the compounds provided herein are provided.

TABLE 1

Antiviral activity of 5-phosphono-pent-2-en-1-yl nucleosides and their alkyloxyalkyl phosphonoesters

| Compounds | HCMV[1] | HSV-1[2] | Vaccinia[3] | Cowpox[4] | HIV-1[5] | VZV[6] | HBV[7] | EBV[8] |
|---|---|---|---|---|---|---|---|---|
| PPen-A | >100 | >30 | >100 | >100 | >100 | >300 | >30 | >4 |
| PPen-C | >100 | >30 | >100 | >100 | >100 | >60 | >30 | ND |
| PPen-G | 68.4 | >30 | >100 | >100 | >100 | 7.2 | >30 | ND |
| PPen-T | >100 | >30 | >100 | >100 | >100 | >300 | >30 | ND |
| PPen-U | >100 | >30 | >100 | >100 | >100 | >300 | >30 | ND |
| HDP-PPen-A | >20 | 17.7 | 39.4 | >20 | >10 | >60 | 1.1; 2.0 | 0.1 |
| HDP-PPen-C | 2.9 | 4.7 | >20 | >20 | 2.5 | ND | 1.7; 6.1 | ND |

TABLE 1-continued

Antiviral activity of 5-phosphono-pent-2-en-1-yl nucleosides
and their alkyloxyalkyl phosphonoesters

| Compounds | HCMV[1] | HSV-1[2] | Vaccinia[3] | Cowpox[4] | HIV-1[5] | VZV[6] | HBV[7] | EBV[8] |
|---|---|---|---|---|---|---|---|---|
| HDP-PPen-G | 0.73 | 5.8; 2.5 | 2.9; 7.5 | 3.4; 10.7 | >10 | 0.15 | 2.4; 2.5 | 48 |
| ODE-PPen-G | ND | 4.6 | ND | ND | ND | ND | ND | ND |
| OLE-PPen-G | ND | 0.68 | ND | ND | ND | ND | ND | ND |
| HDP-PPen-T | 0.64 | 0.90 | >20 | >20 | 1.0 | ND | 3.0; 1.0 | ND |
| HDP-PPen-U | >20 | >30 | >100 | >100 | >10 | ND | >30 | ND |

Effective concentration 50%, $EC_{50}$, μM; [1]AD169, plaque reduction assay in HFF cells. [2]HSV-1, DNA reduction assay in MRC-5 cells, [3]vaccinia WR, plaque reduction assay in HFF cells, [4]cowpox Brighton, plaque reduction assay in HFF cells, [5]HIV-$t_{Lai}$, p24 reduction assay In MT-2 cells, [6]VZV, CPE assay in HFF cells. [7]HBV, DNA reduction assay in 2.2.15 cells, [8]EBV Elisa assay in Daudi cells. Abbreviations: HDP-, hexadecyloxypropyl-; ODE-, octadecyloxyethl-; OLE-, oleyloxyethyl-, ND=Not determined.

In Table 2, activity for further exemplary compounds is provided as follows:

TABLE 2

Antiviral Activity of ODE-and OLE-PPen-G
against human and murine CMV in vitro:

| | $EC_{50}$ (μm) | | $EC_{90}$ (μm) | | $CC_{50}$ (μm) | |
|---|---|---|---|---|---|---|
| | HCMV | MCMV | HCMV | MCMV | HCMV | MCMV |
| ODE-PPen-G | 0.17 | 0.004 | 0.81 | 0.03 | >1 | 0.2 |
| OLE-PPen-G | 0.47 | 0.028 | 0.89 | 0.12 | >1 | >1 |

Table 3 provides in vitro data for the effect of HDP-PPen-A and HDP-PPen-G on hepatitis B mutants resistant to 3TC and adefovir.

TABLE 3

Antiviral Activity Against wild type
HBV and Drug Resistant HBV in vitro

| HBV VIRUS | HDP-PPen-A | HDP-PPen-G |
|---|---|---|
| Wild Type | 9.2 | 8.8 |
| M204V (3TC) | 9.0 | 16 |
| M204I (3TC) | 7.7 | 13 |
| L180M (3TC) | 15 | >100 |
| L180M/M204V (3TC) | 8.1 | >100 |
| N236T (Adefovir dipivoxil) | 10 | 6.3 |

Hepatitis B virus resistance mutation as indicated. Data are $EC_{50}$, μM, for intracellular HBV replicative intermediates (HBV R.I.). Compound in parentheses is the HBV drug to which the mutant is resistant.

The hexadecyloxypropyl ester of PPen-A is fully active against hepatitis B viruses which have become resistant to 3TC (Epivir®) with mutations M204V, M204I, L180M and the double mutant L180M/M204V. HDP-PPen-A is also fully active against HBV resistant to adefovir (Hepsera®) because of the N236T mutation. HDP-PPen-G is active against some 3TC resistant viruses, M204V and M204I, but not against L180M. HDP-PPen-G is fully active against adefovir-resistant HBV having the N236T mutation.

G. Methods of Use of the Compounds and Compositions

Methods of treating, preventing, or ameliorating one or more symptoms of diseases associated with viral infections or inappropriate cell proliferation using the compounds and compositions are provided. In practicing the methods, effective amounts of the compounds or compositions containing therapeutically effective concentrations of the compounds are administered. In certain embodiments, the methods provided herein are for the preventing, or ameliorating one or more symptoms of diseases associated with viral infections, including, but not limited to influenza; hepatitis B and C virus; cytomegalovirus (CMV); herpes infections, such as those caused by Varicella zoster virus, Herpes simplex virus types 1 & 2, Epstein-Barr virus, Herpes type 6 (HHV-6) and type 8 (HHV-8); Varicella zoster virus infections such as shingles or chicken pox; Epstein Barr virus infections, including, but not limited to infectious mononucleosis/glandular; retroviral infections including, but not limited to SIV, HIV-1 and HIV-2; ebola virus; adenovirus and papilloma virus.

In further embodiments, the methods provided herein are for treating, preventing, treating, or ameliorating one or more symptoms of diseases associated with viral infections caused by orthopox viruses, such as variola major and minor, vaccinia, smallpox, cowpox, camelpox, and monkeypox. In certain embodiments, the disease is drug resistant hepatitis B.

In certain embodiments, the methods provided herein are for treating, preventing, or ameliorating one or more symptoms of diseases associated with cell proliferation, including, but not limited to cancers. Examples of cancers include, but are not limited to, lung cancer, head and neck squamous cancers, colorectal cancer, prostate cancer, breast cancer, acute lymphocytic leukemia, adult acute myeloid leukemia, adult non Hodgkin's lymphoma, brain tumors, cervical cancers, childhood cancers, childhood sarcoma, chronic lymphocytic leukemia, chronic myeloid leukemia, esophageal cancer, hairy cell leukemia, kidney cancer, liver cancer, multiple myeloma, neuroblastoma, oral cancer, pancreatic cancer, primary central nervous system lymphoma, and skin cancer.

H. Combination Therapy

The compounds and compositions provided herein may also be used in combination with one or more other active ingredients. In certain embodiments, the compounds may be administered in combination, or sequentially, with another therapeutic agent. Such other therapeutic agents include those known for treatment, prevention, or amelioration of one or more symptoms associated with viral infections or inappropriate cell proliferation. Such therapeutic agents include, but are not limited to, antiviral agents and anti-neoplastic agents.

Recently, it has been demonstrated that the efficacy of a drug against HIV infection can be prolonged, augmented, or restored by administering the compound in combination or alternation with a second, and perhaps third, antiviral compound that induces a different mutation from that caused by the principle drug. Alternatively, the pharmacokinetics, biodistribution, or other parameter of the drug can be altered by such combination or alternation therapy.

In certain embodiments, provided herein are methods of treatment of prevention that encompass administration of a second agent effective for the treatment or prevention of viral infection, such as HIV and/or HCV infection. The second agent can be any agent known to those of skill in the art to be effective for the treatment, prevention or amelioration of viral infections, such as the HIV and/or HCV infection. The second agent can be a second agent presently known to those of skill in the art, or the second agent can be second agent later developed for the treatment, prevention or amelioration of viral infections. In certain embodiments, the second agent is presently approved for the treatment or prevention of HIV and/or HCV.

In certain embodiments, a compound provided herein is administered in combination with one second agent. In further embodiments, a second agent is administered in combination with two second agents. In still further embodiments, a second agent is administered in combination with two or more second agents.

The second antiviral agent for the treatment of HIV, in one embodiment, can be a reverse transcriptase inhibitor (a "RTI"), which can be either a synthetic nucleoside (a "NRTI") or a non-nucleoside compound (a "NNRTI"). In an alternative embodiment, in the case of HIV, the second (or third) antiviral agent can be a protease inhibitor. In other embodiments, the second (or third) compound can be a pyrophosphate analog, or a fusion binding inhibitor.

In some embodiments, compounds for combination or alternation therapy for the treatment of HBV include, but are not limited to 3TC, FTC, L-FMAU, interferon, β-D-dioxolanyl-guanine (DXG), β-D-dioxolanyl-2,6-diaminopurine (DAPD), and β-D-dioxolanyl-6-chloropurine (ACP), famciclovir, penciclovir, BMS-200475, bis pom PMEA (adefovir, dipivoxil); lobucavir, ganciclovir, and ribavarin.

In another embodiment, examples of antiviral agents that can be used in combination or alternation with the compounds disclosed herein for HIV therapy include cis-2-hydroxymethyl-5-(5-fluorocytosin-1-yl)-1,3-oxathiolane (FTC); the (-;)-enantiomer of 2-hydroxymethyl-5-(cytosin-1-yl)-1,3-oxathiolane (3TC); carbovir, acyclovir, foscarnet, interferon, AZT, DDI, DDC, D4T, CS-87 (3'-azido-2',3'-dideoxy-uridine), and β-D-dioxolane nucleosides such as β-D-dioxolanyl-guanine (DXG), β-D-dioxolanyl-2,6-diaminopurine (DAPD), and β-D-dioxolanyl-6-chloropurine (ACP), MKC442 (6-benzyl-1-(ethoxymethyl)-5-isopropyl uracil.

The protease inhibitors include crixivan (Merck), nelfinavir (Agouron), ritonavir (Abbott), saquinavir (Roche), DMP-266 (Sustiva) and DMP-450 (DuPont Merck).

Further compounds that can be administered in combination or alternation with any of the compounds provided herein include (1S, 4R)4-[2-amino-6-cyclopropyl-amino)-9H-purin-9-yl]-2-cyclopentene-1-methanol succinate ("1592", a carbovir analog); 3TC; -β-L-2',3'-dideoxy-3'-thiacytidine; a-APA R18893: a-nitro-anilino-phenylacetamide; A-77003; C2 symmetry-based protease inhibitor; A-75925: C2 symmetry-based protease inhibitor; AAP-BHAP: bisheteroarylpiperazine analog; ABT-538: C2 symmetry-based protease inhibitor; AzddU: 3'-azido-2',3'-dideoxyuridine; AZT: 3'-azido-3'-deoxythymidine; AZT-p-ddI:3'-azido-3'-deoxythymidilyl-(5',5')-2',3'-dideoxyinosinic acid; BHAP: bisheteroarylpiperazine; BILA 1906: N—{1S-[[[3-[2S-{(1,1-dimethylethyl)amino]carbonyl}-4R-]3-pyridinylmethyl)thio]-1-piperidinyl]-2R-hydroxy-1S-(phenylmethyl)propyl]amino] carbonyl]-2-methylpropyl}-2 -quinolinecarboxamide; BILA 2185: N-(1,1-dimethylethyl)-1-[2S-[[2-2,6-dimethyphenoxy)-1-oxoethyl]amino]-2R-hydroxy-4-phenylbutyl]4R-pyridinylthio)-2-piperidine-carboxamide; BM+51.0836: thiazolo-isoindolinone derivative; BMS 186,318: aminodiol derivative HIV-1 protease inhibitor; d4API: 9-[2,5-dihydro-5-(phosphonomethoxy)-2-furanyl]adenine; d4C: 2',3'-didehydro-2',3'-dideoxycytidine; d4T: 2',3'-didehydro-3'-deoxythymidine; ddC; 2',3'-dideoxycytidine; ddI: 2',3'-dideoxyinosine; DMP-266: a 1,4-dihydro-2H-3,1-benzoxazin-2-one; DMP-450: {[4R-(4-a, 5-a, 6-b, 7-b)]-hexahydro-5,6-bis(hydroxy)-1,3-bis(3-amino)phenyl] methyl)-4,7-bis(phenylmethyl)-2H-1,3-diazepin-2-one}-bismesylate; DXG:(-;)-β-D-dioxolane-guanosine; EBU-dM: 5-ethyl-1-ethoxymethyl-6-3,5-dimethylbenzyl)uracil; E-EBU: 5-ethyl-1-ethoxymethyl-6-benzyluracil; DS: dextran sulfate; E-EPSeU: 1-ethoxymethyl) (6-phenylselenyl)-5-ethyluracil; E-EPU: 1-(ethoxymethyl)-(6-phenyl-thio)-5-ethyluracil; FTC:β-2',3'-dideoxy-5-fluoro-3'-thiacytidine (Triangle); HBY097:S-4-isopropoxycarbonyl-6-methoxy-3-(methylthio-methyl)-3,4-dihydroquinoxalin-2(1H)-thione; HEPT:1-[(2-hydroxyethoxy)methyl]-6-(phenylthio)thymine; HIV-1:human immunodeficiency virus type 1; JM2763: 1,1'-(1,3-propanediyl)-bis-1,4,8,11-tetraazacyclotetradecane; JM3100:1,1'-[1,4-phenylenebis-(methylene)]-bis-1,4,8,11-tetraazacyclotetradecane; KNI-272: (2S,3S)-3-amino-2-hydroxy-4-phenylbutyric acid-containing tripeptide; L-697,593;5-ethyl-6-methyl-3-(2-phthalimido-ethyl)pyridin-2(1H)-one; L-735,524:hydroxy-aminopentane amide HIV-1 protease inhibitor; L-697,661: 3-{[(-4,7-dichloro-1,3-benzoxazol-2-yl)methyl]amino}-5-ethyl-6-methylpyridin-2 (1H)-one; L-FDDC: (-;)-β-L-5-fluoro-2',3'-dideoxycytidine; L-FDOC:(-;)-β-L-5-fluoro-dioxolane cytosine; MKC442:6-benzyl-1-ethoxymethyl-5-isopropyluracil (1-EBU); Nevirapine: 11-cyclopropyl-5,11-dihydro-4-methyl-6H-dipyridol[3,2-b:2',3'-e]diazepin-6-one; NSC648400:1-benzyloxymethyl-5-ethyl-6-(alpha-pyridylthio)uracil (E-BPTU); P9941: [2-pyridylacetyl-IlePheAla-y(CHOH)]2; PFA: phosphonoformate; PMEA: 9-(2-phosphonylmethoxyethyl)adenine; PMPA: (R)-9-(2-phosphonyl-methoxypropyl)adenine; Ro 31-8959: hydroxyethylamine derivative HIV-1 protease inhibitor; RPI-312: peptidyl protease inhibitor, 1-[(3s)-3-(n-alpha-benzyloxycarbonyl)-1-asparginyl)-amino-2-hydroxy-4-phenylbutyryl]-n-tert-butyl-1-proline amide; 2720: 6-chloro-3,3-dimethyl-4-(isopropenyloxycarbonyl)-3,4-dihydro-quinoxalin-2(1H)thione; SC-52151: hydroxyethylurea isostere protease inhibitor; SC-55389A: hydroxyethyl-urea isostere protease inhibitor; TIBO R82150: (+)-(5S)-4,5,6,7-tetrahydro-5-methyl-6-(3-methyl-2-butenyl)imidazo[4,5,1-jk][1,4]-benzodiazepin-2(1H)-thione; TIBO 82913: (+)-(5S)-4,5,6,7,-tetrahydro-9-chloro-5-methyl-6-(3-methyl-2-butenyl)imidazo[4,5,1jk]-[1,4]benzo-diazepin-2(1H)-thione; TSAO-m3T:[2',5'-bis-O-(tert-butyldimethylsilyl)-3'-spiro-5'-4'-amino-1',2'-oxathiole-2',2'-dioxide)]-b-D-pentofiaranosyl-N-3-methylthymine; U90152:1-[3-[(1-methylethyl)-amino]-2-pyridinyl]-4-[[5-[(methylsulphonyl)-amino]-1H-indol-2yl]carbonyl]-piperazine; UC: thiocarboxanilide derivatives (Uniroyal); UC-781=N-[4-chloro-3-(3-methyl-2-butenyloxy)phenyl]-2-methyl-3-furancarbothioamide; UC-82=N-[4-chloro-3-(3-methyl-2-butenyloxy)phenyl]-2-methyl-3-thiophenecarbothioamide; VB 11,328: hydroxyethyl-sulphonamide protease inhibitor; VX-478:hydroxyethylsulphonamide protease inhibitor; XM 323: cyclic urea protease inhibitor.

In certain embodiments, suitable second agents include small-molecule, orally bioavailable inhibitors of the HCV enzymes, nucleic-acid-based agents that attack viral RNA, agents that can modulate the host immune response. Exemplary second agents include: (i) current approved therapies (peg-interferon plus ribavirin), (ii) HCV-enzyme targeted compounds, (iii) viral-genome-targeted therapies (e.g., RNA interference or RNAi), and (iv) immunomodulatory agents such as ribavirin, interferon (INF) and Toll-receptor agonists.

In certain embodiments, the second agent is a modulator of the NS3-4A protease. The NS3-4A protease is a heterodimeric protease, comprising the amino-terminal domain of the NS3 protein and the small NS4A cofactor. Its activity is essential for the generation of components of the viral RNA replication complex.

One useful NS3-4A protease inhibitor is BILN 2061 (Ciluprevir; Boehringer Ingelheim), a macrocyclic mimic of peptide product inhibitors. Although clinical trials with BILN 2061 were halted (preclinical cardiotoxicity), it was the first NS3 inhibitor to be tested in humans. See Lamarre et al., 2003, *Nature* 426:186-189, the contents of which are hereby incorporated by reference in their entirety.

Another useful NS3-4A protease inhibitor is VX-950 (Vertex/Mitsubishi), a protease-cleavage-product-derived peptidomimetic inhibitor of the NS3-4A protease. It is believed to be stabilized into the enzyme's active site through a ketoamide. See, e.g., Lin et al., 2005, *J Biol Chem*. Manuscript M506462200 (epublication); Summa, 2005, *Curr Opin Investig Drugs.* 6:831-7, the contents of which are hereby incorporated by reference in their entireties.

In certain embodiments, the second agent is a modulator of the HCV NS5B The RNA-dependent RNA polymerase (RdRp). Contained within the NS5B protein, RdRp synthesizes RNA using an RNA template. This biochemical activity is not present in mammalian cells.

One useful modulator of RdRp is NM283 (Valopicitabine; Idenix/Novartis). NM283, is an oral prodrug (valine ester) of NM107 (2-C-methyl-cytidine) in phase II trials for the treatment or prevention of HCV infection. See, e.g., U.S. Patent Application Publication No. 20040077587, the contents of which are hereby incorporated by reference in their entirety.

Other useful modulators of RdRp include 7-deaza nucleoside analogs. For instance, 7-Deaza-2'-C-methyl-adenosine is a potent and selective inhibitor of hepatitis C virus replication with excellent pharmacokinetic properties. Olsen et al, 2004, *Antimicrob. Agents Chemother.* 48:3944-3953, the contents of which are hereby incorporated by reference in their entirety.

In further embodiments, the second agent is a non-nucleoside modulator of NS5B. At least three different classes of non-nucleoside inhibitors (NNI) of NS5B inhibitors are being evaluated in the clinic.

Useful non-nucleoside modulators of NS5B include JTK-003 and JTK-009. JTK-003 has been advanced to phase II. Useful non-nucleoside modulators of NS5B include the 6,5-fused heterocyclic compounds based on a benzimidazole or indole core. See, e.g., Hashimoto et al., WO 00147883, the contents of which are hereby incorporated by reference in their entirety.

Further useful polymerase NNIs include R803 (Rigel) and HCV-371, HCV-086 and HCV-796 (ViroPharma/Wyeth). Additional useful NNIs include thiophene derivatives that are reversible allosteric inhibitors of the NS5B polymerase and bind to a site that is close to, but distinct from, the site occupied by benzimidazole-based inhibitors. See, e.g., Biswal, et al., 2005, *J. Biol. Chem.* 280, 18202-18210 (2005).

Further useful NNIs for the methods provided herein include benzothiadiazines, such as benzo-1,2,4-thiadiazines. Derivatives of benzo-1,2,4-thiadiazine have been shown to be highly selective inhibitors of the HCV RNA polymerase. Dhanak, et al., 2002, *J. Biol. Chem.* 277:38322-38327, the contents of which are hereby incorporated by reference in their entirety.

Further useful NNIs for the methods provided herein, and their mechanisms, are described in LaPlante et al., 2004 *Angew Chem. Int. Ed. Engl.* 43:4306-4311; Tomei et al, 2003, *J. Virol.* 77:13225-13231; Di Marco et al., 2005, *J. Biol. Chem.* 280:29765-70; Lu, H., WO 2005/000308; Chan et al., 2004, *Bioorg. Med. Chem. Lett.* 14; 797-800; Chan et al., 2004, *Bioorg. Med. Chem. Lett.* 14:793-796; Wang et al., 2003, *J. Biol. Chem.* 278:9489-9495; Love, et al., 2003, *J. Virol.* 77:7575-7581; Gu et al, 2003, *J. Biol. Chem.* 278: 16602-16607; Tomei et al., 2004, *J. Virol.* 78:938-946; and Nguyen et al., 2003, *Antimicrob. Agents Chemother.* 47:3525-3530; the contents of each are hereby incorporated by reference in their entireties.

In a further embodiment, the second agent is an agent that is capable of interfering with HCV RNA such as small inhibitory RNA (siRNA) or a short hairpin RNA (shRNA) directed to an HCV polynucleotide. In tissue culture, siRNA and vector-encoded short hairpin RNA shRNA directed against the viral genome, effectively block the replication of HCV replicons. See, e.g., Randall et al., 2003, *Proc. Natl. Acad. Sci. USA* 100:235-240, the contents of which are hereby incorporated by reference in their entirety.

In a further embodiment, the second agent is an agent that modulates the subject's immune response. For instance, in certain embodiments, the second agent can be a presently approved therapy for HCV infection such as an interferon (IFN), a pegylated IFN, an IFN plus ribavirin or a pegylated IFN plus ribavirin. In certain embodiments, interferons include IFNα, IFNα2a and IFNα2b, and particularly pegylated IFNα2a (PEGASYS®) or pegylated IFNα2b (PEG-INTRON®).

In a further embodiment, the second agent is a modulator of a Toll-like receptor (TLR). It is believed that TLRs are targets for stimulating innate anti-viral response. Suitable TLRs include, bur are not limited to, TLR3, TLR7, TLR8 and TLR9. It is believed that toll-like receptors sense the presence of invading microorganisms such as bacteria, viruses and parasites. They are expressed by immune cells, including macrophages, monocytes, dendritic cells and B cells. Stimulation or activation of TLRs can initiate acute inflammatory responses by induction of antimicrobial genes and pro-inflammatory cytokines and chemokines.

In certain embodiments, the second agent is a polynucleotide comprising a CpG motif. Synthetic oligonucleotides containing unmethylated CpG motifs are potent agonists of TLR-9. Stimulation of dendritic cells with these oligonucleotides results in the production of tumour necrosis factor-alpha, interleukin-12 and IFN-alpha. TLR-9 ligands are also potent stimulators of B-cell proliferation and antibody secretion. One useful CpG-containing oligonucleotide is CPG-10101 (Actilon; Coley Pharmaceutical Group) which has been evaluated in the clinic.

Another useful modulator of a TLR is ANA975 (Anadys). ANA975 is believed to act through TLR-7, and is known to elicit a powerful anti-viral response via induction and the release of inflammatory cytokines such as IFN-alpha.

In another embodiment, the second agent is Celgosivir. Celgosivir is an alpha-glucosidase I inhibitor and acts through host-directed glycosylation. In preclinical studies, celgosivir has demonstrated strong synergy with IFNα plus ribavirin. See, e.g., Whitby et al., 2004, *Antivir Chem Chemother.* 15(3):141-51. Celgosivir is currently being evaluated in a Phase II monotherapy study in chronic HCV patients in Canada.

Further immunomodulatory agents, and their mechanisms or targets, are described in Schetter & Vollmer, 2004, *Curr. Opin. Drug Discov. Dev.* 7:204-210; Takeda et al., 2003,

*Annu. Rev. Immunol.* 21:335-376; Lee et al., 2003, *Proc. Natl Acad. Sci. USA* 100:6646-6651; Hosmans et al., 2004, *Hepatology* 40 (Suppl. 1), 282A; and U.S. Pat. No. 6,924,271; the contents of each are hereby incorporated by reference in their entireties.

In certain embodiments, the compounds provided herein may be administered in combination with one or more anti-cancer agents. Anti-cancer agents for use in combination with the instant compounds include, but are not limited to, an antifolate, a 5-fluoropyrimidine (including 5-fluorouracil), a cytidine analogue such as β-L-1,3-dioxolanyl cytidine or β-L-1,3-dioxolanyl 5-fluorocytidine, antimetabolites (including purine antimetabolites, cytarabine, fudarabine, floxuridine, 6-mercaptopurine, methotrexate, and 6-thioguanine), hydroxyurea, mitotic inhibitors (including CPT-11, Etoposide (VP-21), taxol, and vinca alkaloids such as vincristine and vinblastine, an alkylating agent (including but not limited to busulfan, chlorambucil, cyclophosphamide, ifofamide, mechlorethamine, melphalan, and thiotepa), nonclassical alkylating agents, platinum containing compounds, bleomycin, an anti-tumor antibiotic, an anthracycline such as doxorubicin and dannomycin, an anthracenedione, topoisomerase II inhibitors, hormonal agents (including but not limited to corticosteroids (dexamethasone, prednisone, and methylprednisone), androgens such as fluoxymesterone and methyltestosterone, estrogens such as diethylstilbesterol, antiestrogens such as-tamoxifen, LHRH analogues such as leuprolide, antiandrogens such as flutamide, aminoglutethimide, megestrol acetate, and medroxyprogesterone), asparaginase, carmustine, lomustine, hexamethyl-melamine, dacarbazine, mitotane, streptozocin, cisplatin, carboplatin, levamasole, and leucovorin. The compounds of the present invention can also be used in combination with enzyme therapy agents and immune system modulators such as an interferon, interleukin, tumor necrosis factor, macrophage colony-stimulating factor and colony stimulating factor.

It should be understood that any suitable combination of the compounds provided herein with one or more of the above-mentioned compounds and optionally one or more further pharmacologically active substances are considered to be within the scope of the present disclosure. In another embodiment, the compound provided herein is administered prior to or subsequent to the one or more additional active ingredients.

The following examples are provided for illustrative purposes only and are not intended to limit the scope of the invention.

EXAMPLES

In examples 6, 7 and 8, syntheses of PPen-U 22, PPen-C 23 and PPen-T 24 are described in detail. Mitsunobu reaction with uracil and thymine provided the corresponding diethyl phosphonoesters which were hydrolyzed to give PPen-U 22 and PPen-T 24. A diethyl phosphonoester 20 of PPen-C was obtained from a diethyl phosphonoester 19 of PPen-U. The compound 20 were converted to PPen-C 23 by using TMSBr. Examples 9, 10 and 11 show the syntheses of the HDP derivatives of PPen-U 22, PPen-C 23 and PPen-T 24.

Example 1

Synthesis of (5-Hydroxy-pent-3enyl)-phosphonic acid diethyl ester

A. 2-But-3-ynyloxy-tetrahydro-pyran (2)

A solution of 3-butyn-1-ol 1 (1.00 g, 14.3 mmol) and PPTS (0.72 g, 2.9 mmol) in $CH_2Cl_2$ (20 mL) was treated dropwise with dihydropyran (1.7 mL, 19 mmol) and the resulting mixture was stirred for overnight. The reaction mixture was diluted with $CH_2Cl_2$ (80 mL) and washed with 0.02 N NaOH (50 mL) and brine (100 mL). The organic layer was dried over $MgSO_4$ and concentrated and the residue was purified with 3-5% EtOAc in hexane on silica gel to give 1.90 g of compound 2 (12.3 mmol, 86% yield): $^1H$ NMR ($CDCl_3$) δ 4.63 (t, J=3.4 Hz, 1H), 3.92~3.77 (m, 2H), 3.59~3.45 (m, 2H), 2.47 (td, J=7.1, 2.8 Hz, 2H), 1.96 (t, J=2.5 Hz, 1H), 1.90~1.44 (m, 6H).

B. 5-(Tetrahydro-pyran-2-yloxy)-pent-2-yn-1-ol (3)

A solution of compound 2 (11.0 g, 71.3 mmol) in THF (80 mL) was treated with a 1.6 M solution of n-BuLi in hexane (58 mL, 92.8 mmol) dropwise at 0° C. for 20 min. After 30 min, paraformaldehyde (6.4 g) was added to the reaction mixture at 0° C. After 5 h, the reaction mixture was quenched with aq $NH_4Cl$ at 0° C. and diluted with EtOAc (200 mL) and washed with aq $NH_4Cl$ and brine. The organic layer was dried over $MgSO_4$ and concentrated. The residue was purified with 20% EtOAc in hexanes by silica get column chromatography to give 8.15 g of compound 3 (44.2 mmol, 62% yield): $^1H$ NMR ($CDCl_3$) δ 4.63 (t, J=3.4 Hz, 1H), 4.22 (t, J=2.1 Hz, 2H), 3.91~3.76 (m, 2H), 3.59~3.46 (m, 2H), 2.51 (tt, J=7.1, 2.2 Hz, 2H), 1.86~1.46 (m, 6H).

C. tert-Butyl-diphenyl-[5-(tetrahydro-pyran-2-yloxy)-pent-2-ynyloxy]-silane (4)

A solution of compound 3 and imidazole in $CH_2Cl_2$ was treated with TBDPSCl dropwise at 0° C. for 2 h. The reaction mixture was diluted with $CH_2Cl_2$ (300 mL) and washed with water (200 mL). The organic layer was dried over $MgSO_4$ and concentrated. The residue was purified with 10% EtOAc in hexanes by silica gel column chromatography to give 18.0 g of compound 4 (42.6 mmol, 96% yield): $^1H$ NMR ($CDCl_3$) δ 7.80~7.64 (m, 4H), 7.49~7.34 (m, 6H), 4.63 (t, J=3.6 Hz, 1H), 4.31 (t, J=1.9 Hz, 2H), 3.93~3.83 (m, 1H), 3.77 (dt, J=9.7, 7.1 Hz, 1H), 3.55~3.44 (m, 2H), 2.48 (tt, J=7.1, 2.1 Hz, 2H), 1.89~1.46 (m, 6H), 1.06 (s, 9H).

D. 5-(tert-Butyl-diphenyl-silanyloxy)-pent-3-yn-1-ol (5)

A solution of compound 4 (6.12 g, 14.5 mmol) in MeOH (100 mL) was treated with PPTS (0.36 g, 1.43 mmol) at room temperature for overnight. After concentration, the residue was purified by silica gel column chromatography with 20% EtOAc in hexanes to give 3.84 g of product 5 (11.3 mmol, 78%); $^1H$ NMR ($CDCl_3$) δ 7.80~7.66 (m, 4H), 7.49~7.35 (m, 6H), 4.33 (t, J=1.9 Hz, 1H), 3.60 (t, J=6.0 Hz, 2H), 2.40 (tt, J=2.2, 6.1 Hz, 2H) 1.05 (s, 9H).

E. (5-Bromo-pent-2-ynyloxy)-tert-butyl-diphenyl-silane (6)

A solution of compound 5 (1.09 g, 3.22 mmol) and $CBr_4$ (1.28 g, 3.86 mmol) in $CH_2Cl_2$ (70 mL) was treated with a solution of $Ph_3P$ (1.27 g, 4.84 mmol) in $CH_2Cl_2$ (30 mL) dropwise at −78° C. After 30 min, the reaction mixture was slowly warmed up to room temperature for 2 h and then stirred for overnight. The reaction mixture was poured to the silica gel pad. The filtrate was concentrated to dryness. After concentration, the residue was purified with 0~2% EtOAc in hexanes by silica gel column chromatography to give 1.28 g of product 6 (3.19 mmol, 99% yield); $^1H$ NMR ($CDCl_3$) δ

7.80~7.65 (m, 4H), 7.50~7.32 (m, 6H), 4.34 (t, J=1.9 Hz, 1H), 3.35 (t, J=5.8 Hz, 2H), 2.73 (tt, J=2.1, 6.0 Hz, 2H) 1.08 (s, 9H).

F. [5-(tert-Butyl-diphenyl-silanyloxy)-pent-3-ynyl]-phosphonic acid diethyl ester (7)

A mixture of compound 6 (3.24 g, 80.7 mmol) and triethyl phosphate (40 mL) was refluxed under nitrogen atmosphere for overnight. After evaporation, the residue was purified with 50% EtOAc in hexanes by silica gel column chromatography to give 3.26 g of product 7 (7.90 mmol, 98% yield); $^1$H NMR (CDCl$_3$) δ 7.77~7.64 (m, 4H), 7.46~7.32 (m, 6H), 4.29 (t, J=1.9 Hz, 2H), 4.16~4.02 (m, 4H), 2.50~2.34 (m, 2H), 1.96~1.82 (m, 2H), 1.31 (t, J=7.1 Hz, 6H), 1.04 (s, 9H); $^{31}$P NMR (CDCl$_3$) δ 30.43.

G. [S-(tert-Butyl-diphenyl-silanyloxy)-pent-3-enyl]-phosphonic acid diethyl ester (8)

A mixture of compound 7 (5.00 g, 10.9 mmol) and Lindlar's catalyst (5% palladium on calcium carbonate poisoned with lead) in MeOH was treated with H$_2$ using a balloon. After overnight, the reaction mixture was filtered and concentrated to dryness to give 2.50 g of product 8 (5.5 mmol, 50% yield); $^1$H NMR (MeOH-d$_4$) δ 7.73~7.56 (m, 4H), 7.44~7.32 (m, 6H), 5.68~5.57 (m, 1H), 5.45~5.34 (m, 1H), 4.25 (d, J=6.0 Hz, 2H), 4.08~3.97 (m, 4H), 2.24~2.10 (m, 2H), 1.74~1.61 (m, 2H), 1.26 (t, J=7.1 Hz, 6H), 1.03 (s, 9H); $^{31}$P NMR (MeOH-d$_4$) δ 32.17.

H. (5-Hydroxy-pent-3-enyl)-phosphonic acid diethyl ester (9)

A solution of compound 8 (0.67 g, 1.46 mmol) in acetonitrile (20 mL) was treated with a 1.0 M solution of TBAF in THF (1.7 mL) at 0° C. After 1 h, the reaction mixture was concentrated and purified with 5% MeOH in CH$_2$Cl$_2$ by silica gel column chromatography to give 0.32 g of product 9 (1.44 mmol, 99% yield); $^1$H NMR (CDCl$_3$) δ 5.66~5.47 (m, 2H), 4.16~4.02 (m, 6H), 2.43~2.28 (m, 2H), 1.94~1.79 (m, 2H), 1.32 (t, J=7.1 Hz, 6H); $^{31}$P NMR (CDCL$_3$) δ 33.47.

Example 2

Synthesis of 9-(5-Phosphono-pent-2-en-1-yl)-adenine (13, PPen-A)

A. 9-(5-Phosphono-pent-2-en-1-yl)-adenine diethyl phosphonoester (10)

A solution of adenine (0.49 g, 0.36 mmol) in DMF was added to a flask containing compound 9 (0.32 g, 1.4 mmol). The resulting mixture was treated with Ph$_3$P (0.94 g, 0.36 mmol) and DIAD (0.70 mL, 0.36 mmol) successively at 0° C. After overnight the mixture was concentrated and the residue was purified with 5~10% MeOH in CH$_2$Cl$_2$ by silica gel column chromatography to give 0.20 g of product 10 (0.589 mmol, 42% yield); $^1$H NMR (CDCl$_3$) δ 8.36 (s, 1H), 7.86 (s, 1H), 5.83 (br s, 2H), 5.82~5.61 (m, 2H), 4.86 (d, J=6.6 Hz, 2H), 4.18~4.02 (m, 4H), 2.63~2.49 (m, 2H), 1.88 (dt, J=17.9, 7.4 Hz, 2H), 1.32 (t, J=6.9 Hz, 6H); $^{31}$P NMR (CDCl$_3$) δ 31.71; MS (ESI) m/z 340 (M+H)$^+$.

B. 9-(5-Phosphono-pent-2-en-1-yl)-adenine (13, PPen-A)

A solution of compound 10 (0.300 g, 0.884 mmol) in acetonitrile was treated with TMSBr (5 mL) at room temperature for overnight. After concentration, the residue was dissolved in water (20 mL) and the resulting mixture was stirred for 1 h. The reaction mixture was concentrated to dryness. The residue was dissolved in water (4 mL) and adjusted to ca. pH 8. The resulting mixture was loaded to the column containing DOWEX-1X2 resin and purified with gradient eluent (0 M to 0.25 M HCO$_2$H) to give 0.180 g of product 13 (0.636 mmol, 72% yield); $^1$H NMR (MeOH-d$_4$) δ 8.20 (s, 1H), 8.13 (s, 1H), 5.74~5.62 (m, 1H), 5.53~5.41 (m, 1H), 4.78 (d, J=6.9 Hz, 1H), 2.33~2.19 (m, 2H), 1.57~1.43 (m, 2H); $^{31}$P NMR (DMSO-d$_6$) δ 26.31; MS (ESI) m/z 284 (M+H)$^+$, 282 (M−H)$^-$.

Example 3

Synthesis of 9-(5-Phosphono-pent-2-en-1-yl)-guanine (15, PPen-G)

A. 2-amino-6-chloro-9-(5-Phosphono-pent-2-en-1-yl)-purine diethyl phosphonoester (11)

Prepared from 2-amino-6-chloropurine and compound 9 using the procedure from Example 2A. $^1$H NMR (CDCl$_3$) δ 7.76 (s, 1H), 5.75 (br s, 2H), 5.72~5.48 (m, 2H), 4.67 (d, J=6.1 Hz, 2H), 4.17~4.01 (m, 4H), 2.74~2.56 (m, 2H), 1.94~1.78 (m, 2H), 1.30 (t, J=7.1 Hz, 6H); $^{31}$P NMR (CDCl$_3$) δ 32.37; MS (ESI) m/z 374 (M+H)$^+$, 372 (M−H)$^-$.

B. 9-(5-Phosphono-pent-2-en-1-yl)-guanine diethyl phosphonoester (12)

A solution of compound 11 (0.200 g, 0.535 mmol) in 30 mL of 88% HCO$_{2H}$ was stirred at 100° C. for 8 h. After concentration, the residue was purified with 10% MeOH in CH$_2$Cl$_2$ by silica gel column chromatography to give 0.170g of product 12 (0.478 mmol, 89% yield); $^1$H NMR (MeOH-d$_4$) δ 8.97 (s, 1H), 5.90~5.77 (m, 1H), 5.75~5.63 (m, 1H), 4.89 (d, J=7.1 Hz, 1H), 4.17~4.04 (m, 4H), 2.70~2.50 (m, 2H), 2.06~1.87 (m, 2H), 1.33 (t, J=6.9 Hz, 6H); $^{31}$P NMR (CDCl$_3$) δ 33.48; MS (ESI) m/z 356 (M+H)$^+$, 354 (M−H)$^-$.

C. 9-(5-Phosphono-pent-2-en-1-yl)-guanine (15, PPen-G)

See the procedure for the preparation of compound 13. The titled compound 15 was obtained on 0.563 mmol-scale in 95% yield; $^1$H NMR (MeOH-d$_4$) δ 8.71 (s, 1H), 5.84~5.73 (m, 1H), 5.54~5.48 (m, 1H), 4.74 (d, J=6.9 Hz, 1H), 2.44~2.29 (m, 2H), 1.79~1.65 (m, 2H); $^{31}$P NMR (MeOH-d$_4$) δ 29.97; MS (ESI) m/z 300 (M+H)$^+$, 298 (M−H)$^-$.

Example 4

Synthesis of 9-(5-Phosphono-pent-2-en-1-yl)-adenine mono-(3-hexadecyloxy-1-propyl) phosphonoester (16, HDP-PPen-A)

A. 9-(5-Phosphono-pent-2-en-1-yl)-adenine mono-(3-hexadecyloxy-1-propyl) phosphonoester (16)

A solution of compound 13 (0.120 g, 0.424 mmol), 3-hexadecyloxy-propan-1-ol (HDPOH) (0.191 g, 0.64 mmol) and DMAP (0.078 g, 0.64 mmol) in DMF (10 mL) was treated with DCC (0.262 g, 1.26 mmol) at room temperature. The reaction mixture was warmed up to 80° C. and stirred for overnight. After concentration, the residue was purified with a gradient mixture of chloroform, methanol, ammonia water and water (80:20:1:1 to 100:40:3:3) by silica gel column chromatography to give 0.065 g of product 16 (0.115 mmol, 27% yield); $^1$H NMR (MeOH-d$_4$) δ 8.21 (s, 1H), 8.19 (s, 1H) 5.84~5.74 (m, 1H), 5.65~5.57 (m, 1H), 4.92 (d, J=7.0 Hz, 2H), 3.94 (q, J=6.2 Hz, 2H), 3.52 (t, J=6.2 Hz, 2H), 3.37 (t, J=6.6 Hz, 2H), 2.58~2.44 (m, 2H), 1.90~1.78 (m, 2H), 1.74~1.62 (m, 2H), 1.54~1.43 (m, 2H), 1.36~1.14 (m, 12H), 0.89 (t, J=7.0 Hz, 3H); $^{31}$P NMR (MeOH-d$_4$) δ 25.89; MS (ESI) m/z 566 (M+H)$^+$, 564 (M−H)$^−$.

Example 5

Synthesis of 9-(5-Phosphono-pent-2-en-1-yl)-guanine mono-(3-hexadecyloxy-1-propyl) phosphonoester (18, HDP-PPen-G)

A. 2-amino-6-chloro-9-(5-Phosphono-pent-2-en-1-yl)-purine (14)

See the procedure for the preparation of compound 13. The titled compound 14 was obtained from compound 11 on 0.576 mmol-scale. Without further purification, the compound 14 was used for the next reaction; $^1$H NMR (MeOH-d$_4$) δ 9.09 (s, 1H), 5.93~5.81 (m, 1H), 5.78~5.63 (m, 1H), 4.91 (d, J=7.4 Hz, 1H), 2.72~2.54 (m, 2H), 1.96~1.81 (m, 2H); $^{31}$P NMR (MeOH-d$_4$) δ 30.23.

B. 2-amino-6-chloro-9-(5-Phosphono-pent-2-en-1-yl)-purine mono-(3-hexadecyloxy-1-propyl) phosphonoester (17)

See the procedure for the preparation of compound 16. The titled compound 17 was obtained on 0.598 mmol-scale in 56% yield; $^1$H NMR (MeOH-d$_4$) δ 7.79 (s, 1H) 5.76~5.68 (m, 1H), 5.57~5.49 (m, 1H), 4.72 (d, J=7.3 Hz, 2H), 3.95 (q, J=6.6 Hz, 2H), 3.53 (t, J=6.2 Hz, 2H), 3.39 (t, J=6.6 Hz, 2H), 2.62~2.52 (m, 2H), 1.90~1.82 (m, 2H), 1.74~1.64 (m, 2H), 1.56~1.46 (m, 2H), 1.36~1.12 (m, 12H), 0.89 (t, J=6.6 Hz, 3H); $^{31}$P NMR (MeOH-d$_4$) δ 26.46.

C. 9-(5-Phosphono-pent-2-en-1-yl)-guanine mono-(3-hexadecyloxy-1-propyl) phosphonoester (18, HDP-PPen-G)

A solution of compound 17 (0.200 g, 0.333 mmol) in 88% HCO$_2$H (40 mL) was stirred at 100° C. for overnight. After concentration, the residue was purified with a mixture of chloroform, methanol, ammonia water and water (80:20:1:1 to 70:58:8:8) to give 0.120 g of product 18 (0.206 mmol, 62% yield); $^1$H NMR (MeOH-d$_4$) δ 7.75 (s, 1H) 5.76~5.66 (m, 1H), 5.56~5.48 (m, 1H), 4.71 (d, J=7.3 Hz, 2H), 3.94 (q, J=5.9 Hz, 2H), 3.53 (t, J=6.6 Hz, 2H), 3.39 (t, J=6.6 Hz, 2H), 2.62~2.52 (m, 2H), 1.90~1.82 (m, 2H), 1.72~1.62 (m, 2H), 1.54~1.47 (m, 2H), 1.34~1.22 (m, 12H), 0.89 (t, J=7.0 Hz, 3H); $^{31}$P NMR (MeOH-d$_4$) δ 26.14; MS (ESI) m/z 582 (M+H)$^+$, 580 (M−H)$^−$.

Example 6

Synthesis of 1-(5-Phosphono-pent-2-en-1-yl)-uracil (22, PPen-U)

A. 1-(5-Phosphono-pent-2-en-1-yl)-uracil diethyl phosphonoester (19)

A solution of compound 9 (0.20 g, 0.90 mmol), 3-benzoyl-uracil (0.24 g, 1.11 mmol) and Ph$_3$P (0.29 g, 1.1 mmol) in DMF was treated with DIAD (0.21 mL, 1.1 mmol) dropwise at 0° C. After 2 h, the reaction mixture was concentrated and purified with 2% MeOH in CH$_2$Cl$_2$ by silica gel column chromatography. The benzoyl-protected intermediate was dissolved in 2 N ammonia in MeOH (50 mL) and stirred for overnight. The resulting mixture was concentrated and purified with 5% MeOH in CH$_2$Cl$_2$ by silica gel column chromatography to give 0.23 g of product 19 (0.73 mmol, 81% yield); $^1$H NMR (CDCl$_3$) δ 8.66 (br s, 1H), 7.31 (d, J=8.1 Hz, 1H), 5.76~5.66 (m, 1H), 5.69 (dd, J=7.7, 2.0 Hz, 1H), 4.41 (d, J=7.0 Hz, 2H), 4.16~4.02 (m, 4H), 2.53~2.42 (m, 2H), 1.89~1.80 (m, 2H), 1.32 (t, J=7.0 Hz, 3H); $^{31}$P NMR (CDCl$_3$) δ 31.80; MS (ESI) m/z 317 (M+H)$^+$, 315 (M−H)$^−$.

A. 1-(5-Phosphono-pent-2-en-1-yl)-uracil (22, PPen-U)

See the procedure for the preparation of compound 13. The titled compound 22 was obtained on 1.26 mmol-scale in 98% yield; $^1$H NMR (DMSO-d$_6$) δ 11.23 (s, 1H), 7.69 (d, J=7.6 Hz, 1H), 5.68~5.57 (m, 1H), 5.52 (d, J=6.7 Hz, 1H), 5.39~5.18 (m, 1H), 4.28 (d, J=6.6 Hz, 2H), 2.36~2.22 (m, 2H), 1.64~1.51 (m, 2H); $^{31}$P NMR (DMSO-d$_6$) δ 26.38; MS (ESI) m/z 261 (M+H)$^+$, 259 (M−H)$^−$.

Example 7

Synthesis of 1-(5-Phosphono-pent-2-en-1-yl)cytosine (23, PPen-C)

A. 1-(5-Phosphono-pent-2-en-1-yl)-cytosine diethyl phosphonoester (20)

A solution of compound 19 (0.73 g, 2.3 mmol), TEA (0.97 mL, 7.0 mmol) and DMAP (0.28 g, 2.3 mmol) in acetonitrile was treated with 2,4,6-triisopropylbenzenesulfonyl chloride (2.1 g, 6.9 mmol) at room temperature for 3 h. Ammonia water (5 mL) was added to the reaction mixture. The resulting mixture was stirred for 1 h. After concentration, the residue was purified with a mixture of chloroform, methanol, ammonia water and water (240:20:1:1) by silica gel column chromatography to give 0.55 g of product 20 (1.74 mmol, 75% yield); $^1$H NMR (CDCl$_3$) δ 7.34 (d, J=7.1 Hz, 1H), 5.80 (d, J=7.4 Hz, 1H), 5.72~5.61 (m, 1H), 5.56~5.46 (m, 1H), 4.44 (d, J=6.9 Hz, 2H), 4.16~4.02 (m, 4H), 2.54~2.39 (m, 2H), 2.17 (br s, 2H), 1.91~1.78 (m, 2H), 1.32 (t, J=7.1 Hz, 6H); $^{31}$P NMR (CDCl$_3$) δ 32.06; MS (ESI) m/z 316 (M+H)$^+$, 314 (M−H)$^−$.

B. 1-(5-Phosphono-pent-2-en-1-yl)-cytosine (23, PPen-C)

See the procedure for the preparation of compound 13. The titled compound 23 was obtained on 1.30 mmol-scale in 71% yield; $^1$H NMR (DMSO-d$_6$) δ 7.52 (d, J=7.1 Hz, 1H), 7.04 (br s, 1H), 6.98 (br s, 1H), 5.62 (d, J=7.7 Hz, 1H), 5.66~5.53 (m, 1H), 5.37~5.26 (m, 1H), 4.26 (d, J=6.9 Hz, 2H), 2.37~2.23 (m, 2H), 1.63~1.50 (m, 2H); $^{31}$p NMR (DMSO-d$_6$) δ 26.14; MS (ESI) m/z 260 (M+H)$^+$, 258 (M−H)$^−$.

Example 8

Synthesis of 1-(5-Phosphono-pent-2-en-1-yl)-thymine (24, PPen-T)

A. 1-(5-Phosphono-pent-2-en-1-yl)-thymine diethyl phosphonoester (21)

See the procedure for the preparation of compound 19. The titled compound 21 was obtained on 1.44 mmol-scale in 78% yield; $^1$H NMR (CDCl$_3$) δ 8.46 (br s, 1H), 7.11 (s, 1H), 5.78~5.66 (m, 1H), 5.52~5.41 (m, 1H), 4.38 (d, J=6.6 Hz, 2H), 4.20~4.02 (m, 4H), 2.55~2.41 (m, 2H), 1.91 (s, 3H), 1.91~1.78 (m, 2H), 1.33 (t, J=7.1 Hz, 6H); $^{31}$P NMR (CDCL$_3$) δ 31.84; HRMS obsd, m/z 330.1352, calcd for C$_{14}$H$_{23}$N$_2$O$_5$P, m/z 330.1339 M$^+$.

B. 1-(5-Phosphono-pent-2-en-1-yl)-thymine (24, PPen-T)

See the procedure for the preparation of compound 13. The titled compound 24 was obtained on 1.12 mmol-scale in 85% yield; $^1$H NMR (MeOH-d$_4$) δ 7.41 (s 1H), 5.80~5.65 (m, 1H), 5.53~5.41 (m, 1H), 4.39 (d, J=5.5 Hz, 2H), 2.56~2.40 (m, 2H), 1.85 (s, 3H), 1.85~1.74 (m, 2H); $^{31}$P NMR (MeOH-d$_4$) δ 30.40; HRMS obsd, m/z 274.0727, calcd for C$_{10}$H$_{15}$N$_2$O$_5$P, m/z 274.0713 M$^+$.

Example 9

Synthesis of 1-(5-Phosphono-pent-2-en-1-yl)-uracil mono-(3-hexadecyloxy-1-propyl) phosphonoester (25, HDP-PPen-U)

See the procedure for the preparation of compound 16. The titled compound 25 was obtained on 0.50 mmol-scale in 44% yield; $^1$H NMR (MeOH-d$_4$) δ 7.62 (d, J=8.0 Hz, 1H), 5.82~5.71 (m, 1H), 5.65 (d, J=8.0 Hz, 1H), 5.50~5.37 (m, 1H), 4.44 (d, J=5.8 Hz, 2H), 3.93 (q, J=6.3 Hz, 2H), 3.53 (t, J=6.3 Hz, 2H), 3.41 (t, J=6.6 Hz, 2H), 2.50~2.36 (m, 2H), 1.90~1.81 (m, 2H), 1.70~1.48 (m, 4H), 1.40~1.20 (m, 12H), 0.89 (t, J=6.2 Hz, 3H); $^{31}$P NMR (MeOH-d$_4$) δ 25.90; MS (ESI) m/z 543 (M+H)$^+$, 541 (M−H)$^-$.

Example 10

Synthesis of 1-(5-Phosphono-pent-2-en-1-yl)-cytosine mono-(3-hexadecyloxy-1-propyl) phosphonoester (26, HDP-PPen-C)

See the procedure for the preparation of compound 16. The titled compound 17 was obtained on 0.58 mmol-scale in 38% yield; $^1$H NMR (MeOH-d$_4$) δ 7.86 (d, J=7.4 Hz, 1H), 5.96 (d, J=7.6 Hz, 1H), 5.84~5.72 (m, 1H), 5.52~5.51 (m, 1H), 4.50 (d, J=6.6 Hz, 2H), 3.92 (q, J=6.3 Hz, 2H), 3.53 (t, J=6.0 Hz, 2H), 3.41 (t, J=6.6 Hz, 2H), 2.49~2.35 (m, 2H), 1.91~1.80 (m, 2H), 1.70~1.45 (m, 4H), 1.36~1.22 (m, 12H), 0.89 (t, J=6.6 Hz, 3H); $^{31}$P NMR (MeOH-d$_4$) δ 25.93; HRMS (xx) obsd, m/z 541.3645, calcd for C$_{28}$H$_{52}$N$_3$O$_5$P, m/z 541.3639 M$^+$.

Example 11

Synthesis of 1-(5-Phosphono-pent-2-en-1-yl)-thymine mono-3-hexadecyloxy-1-propyl) phosphonoester (27, HDP-PPen-T)

See the procedure for the preparation of compound 16. The titled compound 17 was obtained on 0.58 mmol-scale in 15% yield; $^1$H NMR (MeOH-d$_4$) δ 7.44 (d, J=1.1 Hz, 1H), 5.80~5.69 (m, 1H), 5.47~5.36 (m, 1H), 4.42 (d, J=6.9 Hz, 2H), 3.92 (q, J=6.3 Hz, 2H), 3.53 (t, J=6.3 Hz, 2H), 3.41 (t, J=6.6 Hz, 2H), 2.50~2.36 (m, 2H), 1.91~1.81 (m, 2H), 1.87 (d, J=1.1 Hz, 3H), 1.70~1.48 (m, 4H), 1.35~1.24 (m, 12H), 0.89 (t, J=6.6 Hz, 3H); $^{31}$P NMR (MeOH-d$_4$) 825.62; HRMS (xx) obsd, m/z 556.3643, calcd for C$_{29}$H$_{53}$N$_2$O$_6$P, m/z 556.3636 M$^+$.

Since modifications will be apparent to those of skill in the art, it is intended that the invention be limited only by the scope of the appended claims.

What is claimed is:

1. A compound of Formula IA or IB:

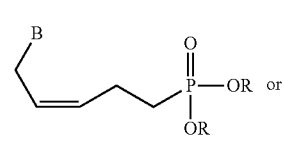

Formula IA

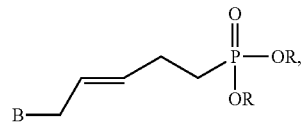

Formula IB or a pharmaceutically acceptable salt thereof,
wherein each R is independently hydrogen, a monovalent cation or a lipophilic group and B is a purine or pyrimidine base or an analog thereof, wherein at least one R is a lipophilic group other than methyl or ethyl.

2. The compound of claim 1, wherein the compound has formula

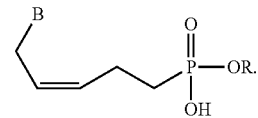

3. The compound of claim 1, wherein R is hydrogen, a monovalent cation, a substituted or unsubstituted C$_8$-C$_{24}$ alkyl or substituted or unsubstituted C$_8$-C$_{24}$ alkenyl having from 1 to 6 double bonds, wherein substituents when present are selected from one or more halogen, alkyl, —OH, —SH, cycloalkyl, or epoxide.

4. The compound of claim 1, wherein R has formula:

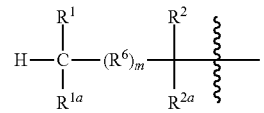

wherein:
R$^1$ and R$^{1a}$ are independently —H, —O(C$_1$-C$_{24}$)alkyl, —O(C$_1$-C$_{24}$)alkenyl, —O(C$_1$-C$_{24}$)acyl, —S(C$_1$-C$_{24}$) alkyl, —S(C$_1$-C$_{24}$)alkenyl, or —S(C$_1$-C$_{24}$)acyl, wherein at least one of R$^1$ and R$^{1a}$ are not —H, and wherein the alkenyl or acyl moieties optionally have 1 to 6 double bonds,
R$^2$ and R$^{2a}$ are independently —H, —O(C$_1$-C$_7$)alkyl, —O(C$_1$-C$_7$)alkenyl, —S(C$_1$-C$_7$)alkyl, —S(C$_1$-C$_7$)alkenyl, —O(C$_1$-C$_7$)acyl, —S(C$_1$-C$_7$)acyl, —N(C$_1$-C$_7$) acyl, —NH(C$_1$-C$_7$)alkyl, —N((C$_1$-C$_7$)alkyl)$_2$, oxo, halogen, —NH$_2$, —OH, or —SH;
R$^6$, when present, is:

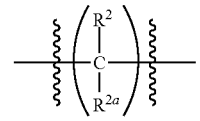

m is an integer from 0 to 6;
and wherein R$^1$, R$_{1a}$, R$_2$, R$^{2a}$, and R$^{7a}$ are optionally substituted with one to four substituents, each independently selected from alkyl, alkenyl, alkynyl, halo, hydroxyl, pseudohalo, amino, nitro, cycloalkyl, heterocyclyl, aryl and heteroaryl.

5. The compound of claim 1, wherein R has formula:

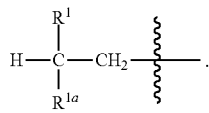

6. The compound of claim 1, wherein R has formula:

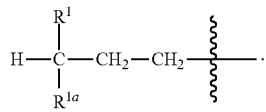

7. The compound of claim 1, wherein R has formula:

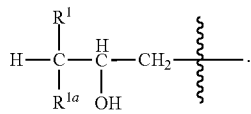

8. The compound of claim 1, wherein R is hexadecyloxypropyl, octadecyloxypropyl, or octadecyloxyethyl.

9. The compound of claim 1, wherein R is acetyl, valyl, dipivoxil, bis(pivaloyloxymethyl) or disoproxil.

10. The compound of claim 1, wherein B is

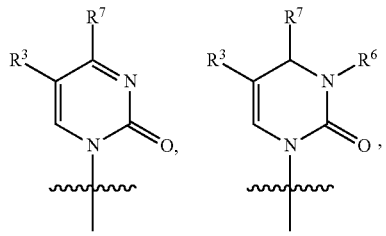

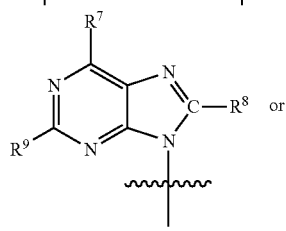

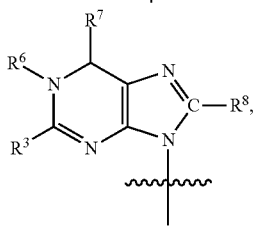

wherein $R^3$ is H, $C_{1-6}$ alkyl, $C_{2-6}$ alkenyl, $C_{2-6}$ alkynyl, $C_{3-6}$ cycloalkyl, hydroxy, halo, aryl or heteroaryl;

$R^6$ is H or $C_{1-6}$ alkyl, $C_{2-6}$ alkenyl, $C_{2-6}$ alkynyl or cycloalkyl;
$R^7$ is H, hydroxy, halo, $C_{1-6}$ alkyl, $C_{2-6}$ alkenyl, $C_{2-6}$ alkynyl, cycloalkyl or $NR^4R^5$;
$R^8$ is H, $C_{1-6}$ alkyl, $C_{2-6}$ alkenyl, $C_{2-6}$ alkynyl or cycloalkyl;
$R^9$ is H, $C_{1-6}$ alkyl, $C_{2-6}$ alkenyl, $C_{2-6}$ alkynyl, cycloalkyl, halo or $NR^4R^5$; and
$R^4$ and $R^5$ are each independently H, $C_{1-6}$ alkyl, $C_{2-6}$ alkenyl, $C_{2-6}$ alkynyl, or $C_{3-6}$ cycloalkyl.

11. The compound of claim 1, wherein, B is thymin-1-yl, cytosine-1-yl, uracil-1-yl, adenine-9-yl or guanine-9-yl.

12. The compound of claim 1, wherein B is selected from:

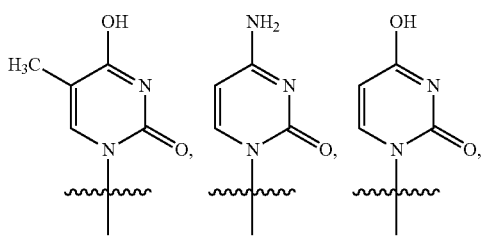

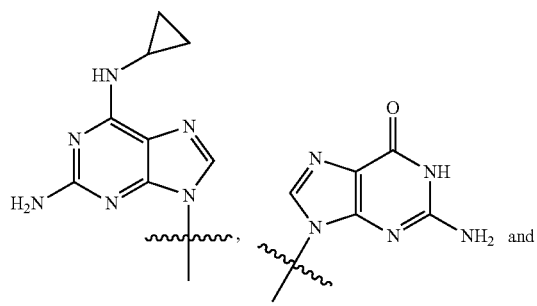

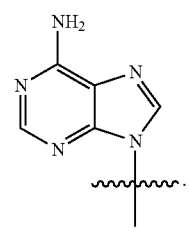

13. The compound of claim 1, wherein the compound is selected from 5-phosphono-pent-2-en-1-yl adenine, 5-phosphono-pent-2-en-1-yl cytosine, 5-phosphono-pent-2-en-1-yl guanine, 5-phosphono-pent-2-en-1-yl thymine and 5-phosphono-pent-2-en-1-yl uracil.

14. The compound of claim 1, wherein the compound is selected from:

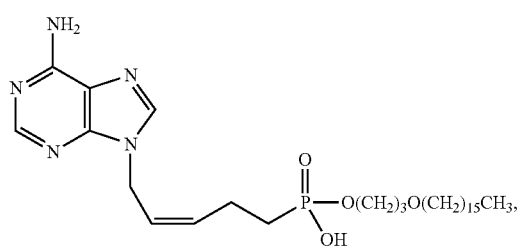

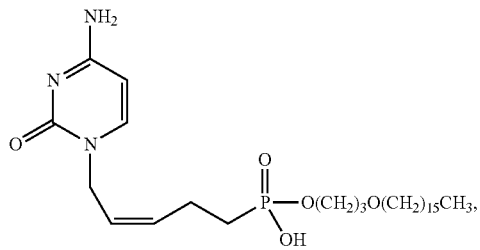

-continued

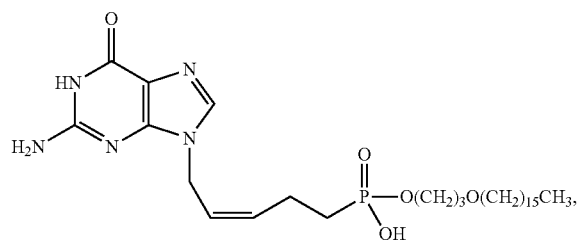
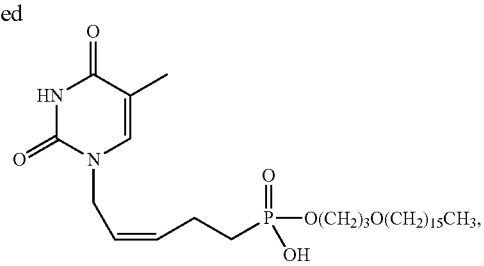
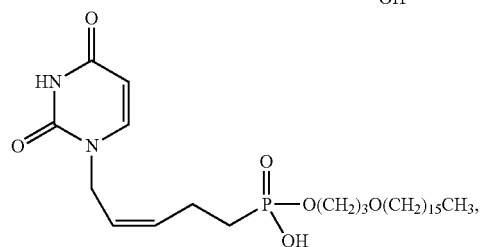
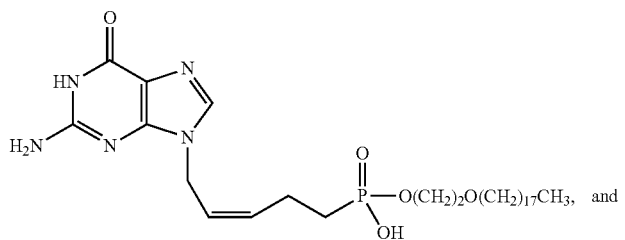
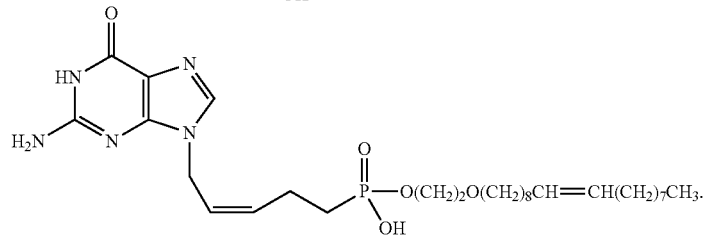

15. A pharmaceutical composition comprising a compound of claim 1 and a pharmaceutically acceptable carrier.

16. A method for treating, a viral infection, wherein the method comprises administering an effective amount of a compound of claim 1.

17. The method of claim 16, wherein the viral infection is a caused by influenza, hepatitis B virus, hepatitis C virus, cytomegalovirus, Varicella zoster virus, Herpes simplex virus types and 2, Epstein-Barr virus, Herpes type 6 and type 8, Varicella zoster virus, Epstein Barr virus infections, retroviral infections, orthopox viruses, vaccinia, ebola virus, adenovirus and papilloma virus.

18. The method of claim 16, wherein the viral infection is drug resistant Hepatitis B.

* * * * *